United States Patent
Boyle et al.

(10) Patent No.: US 6,946,468 B1
(45) Date of Patent: Sep. 20, 2005

(54) 3-MERCAPTOPYRROLIDINES AS FARNESYL PROTEIN TRANSFERASE INHIBITORS

(75) Inventors: Francis Thomas Boyle, Macclesfield (GB); James Michael Wardleworth, Macclesfield (GB)

(73) Assignee: Zeneca Limited, London (GB)

( * ) Notice: Subject to any disclaimer, the term of this patent is extended or adjusted under 35 U.S.C. 154(b) by 0 days.

(21) Appl. No.: 09/242,461

(22) PCT Filed: Aug. 13, 1997

(86) PCT No.: PCT/GB97/02212
§ 371 (c)(1),
(2), (4) Date: Feb. 17, 1999

(87) PCT Pub. No.: WO98/07692
PCT Pub. Date: Feb. 26, 1998

(30) Foreign Application Priority Data

Aug. 17, 1996 (GB) ............................................. 9617302
Jan. 24, 1997 (GB) ............................................. 9701417

(51) Int. Cl.$^7$ ...................... A16K 31/495; A16K 31/50; C07D 403/00; A61P 35/00
(52) U.S. Cl. .................. 514/254.01; 514/343; 514/359; 514/365; 514/423; 514/424; 544/372; 546/278.4; 548/200; 548/260; 548/531; 548/556
(58) Field of Search ...................... 514/254.01; 544/372

(56) References Cited

U.S. PATENT DOCUMENTS

| | | | |
|---|---|---|---|
| 5,185,248 A | 2/1993 | Barbacid et al. ............... | 435/15 |
| 5,929,077 A * | 7/1999 | Leftheris ...................... | 514/255 |
| 6,541,491 B1 | 4/2003 | Davies et al. ............... | 514/340 |

FOREIGN PATENT DOCUMENTS

| | | |
|---|---|---|
| EP | 0 126 587 | 11/1984 |
| EP | 0 182 213 | 5/1986 |
| EP | 0 272 456 | 6/1988 |
| EP | 0 280 771 | 9/1988 |
| EP | 0 442 497 | 8/1991 |
| EP | 0 443 883 | 8/1991 |
| EP | 0 508 682 | 10/1992 |
| EP | 0 518 558 | 12/1992 |
| EP | 0 521 524 | 1/1993 |
| EP | 0 537 007 | 4/1993 |
| EP | 0 560 613 | 9/1993 |
| EP | 0 562 855 | 9/1993 |
| EP | 0 581 500 | 2/1994 |
| EP | 0 581 501 | 2/1994 |
| EP | 0 581 502 | 2/1994 |
| EP | 0 590 885 | 4/1994 |
| EP | 0 592 167 | 4/1994 |
| EP | 0 618 221 | 10/1994 |
| EP | 0 696 593 | 2/1996 |
| JP | 60233076 | 11/1985 |
| JP | 03115285 | 5/1991 |
| JP | 04368386 | 12/1992 |
| JP | 05078360 | 3/1993 |
| JP | 05239058 | 9/1993 |
| WO | WO 92/17479 | 10/1992 |
| WO | WO 92/17480 | 10/1992 |
| WO | WO 93/15078 | 8/1993 |
| WO | WO 93/19070 | 9/1993 |
| WO | WO 93/21186 | 10/1993 |
| WO | WO 94/04561 | 3/1994 |
| WO | WO 95/00497 | 1/1995 |
| WO | WO 95/09000 | 4/1995 |
| WO | WO 95/09001 | 4/1995 |
| WO | WO 95/25086 | 9/1995 |
| WO | WO 96/09821 | 4/1996 |
| WO | WO 97/05135 | 2/1997 |
| WO | 97/06138 | 2/1997 |

OTHER PUBLICATIONS

Ayral–Kaloustian et al., Ras Farnesyltransferase Inhibitors, Annual Reports in Medicinal Chemistry, vol. 31, pp. 171–180, 1996.*

Evans, B., et al., "Nanomolar–Affinity, Non–Peptide Oxytocin Receptor Antagonists," J. Med. Chem. 36(25):3993–4005 (1993).

(Continued)

Primary Examiner—Brenda Coleman
(74) Attorney, Agent, or Firm—Morgan, Lewis & Bockius LLP

(57) ABSTRACT

The present invention relates to inhibitors of ras farnesylation of the Formula I

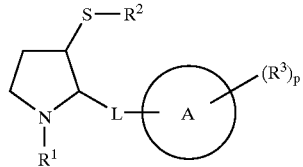

Formula I wherein:

$R^1$ is for example H and further values as defined in the specification; $R^2$ is for example H and further values as defined in the specification; $R^3$ is for example H or a substituent having values as defined in the specification; p is 0–3 in which $R^3$ values can be the same or different; L is a linking moiety for example —$CH_2$—NH— and further values as defined in the specification; A is selected from phenyl; naphthyl; a 5–10 membered monocyclic or bicyclic heteroaryl ring containing upto 5 heteroatoms where the heteroatoms are independently selected from O, N & S; or a —S—S— dimer thereof when $R^2$=H; or a N-oxide or a pharmaceutically-acceptable salt, prodrug or solvate thereof. Processes for their preparation their use as therapeutic agents and pharmaceutical compositions containing them.

9 Claims, No Drawings

OTHER PUBLICATIONS

Garcia, Ana M., et al., "Peptidomimetic Inhibitors of Ras Farnesylation and Function in Whole Cells," *J. Biol. Chem.* 268:18415–18418 (1993).

Graham, Samuel L., et al., "Pseudopeptide Inhibitors of Ras Farnesyl–Protein Transferase," *J. Med. Chem.* 37:725–730 (1994).

Kemp, D.S., et al., "Studies of N–Terminal Templates for α–Helix Formation: Synthesis and Conformational Analysis of(2S,5S,8S,11S)–1–Acetyl–1,4–diaza–3–keto–5–carboxy–10–thiatricyclo[2.8.10$^{4.8}$]– tridecane (Ac–Hel$_1$–OH)," *J. Org. Chem.* 56:6672–6682 (1991).

Kohl, Nancy E., et al., "Selective Inhibition of ras–Dependent Transformation by a Farnesyl–transferase Inhibitor," *SCIENCE* 260:1934–1937 (1993).

Lern, Edwina C., et al., "Ras CAAX Peptidomimetic FTI–277 Selectivity Blocks Oncogenic Ras Signaling by Inducing Cytoplasmic Accumulation of Inactive Ras–Raf Complexes," *J. of Biol. Chem.* 270:26802–26806 (1995).

Magolda, R.L.., et al., "Design and Synthesis of Conformationally Restricted Phospholids as Phospholipase A2 Inhibitors," *J. Cellular Biochemistry* 40:371–386 (1989).

Matsumura, H., et al., "An Efficient Synthesis of (2S, 4S)–2–Substituted 4–Mercaptopyrrolidine Derivatives," *Heterocycles* 41:No. 1, 147–159 (1995).

Sunagawa, M., et al., "A Novel Carbapenem Antibiotic, SM–7338 Structure–Activity Relationships," *J. Antibiotics* vol. XLIII No. 5, pp. 519–532 (1990).

Sunagawa, M., et al., "Synthesis and Antibacterial Activity of Novel Carbapenems with a Catechol or Hydroxypyridone Moiety," *J. Antibiotics* 47(11):1354–1358 (1994).

* cited by examiner

3-MERCAPTOPYRROLIDINES AS FARNESYL PROTEIN TRANSFERASE INHIBITORS

This application is a national stage entry under 35 U.S.C. § 371 of PCT/GB97/02212, filed on Aug. 13, 1996.

This invention relates to compounds that inhibit farnesylation of mutant ras gene products through inhibition of the enzyme farnesyl-protein transferase (FPTase). The invention also relates to methods of manufacturing the compounds, pharmaceutical compositions and methods of treating diseases, especially cancer, which are mediated through farnesylation of ras.

Cancer is believed to involve alteration in expression or function of genes controlling cell growth and differentiation. Whilst not wishing to be bound by theoretical considerations the following text sets out the scientific background to ras in cancer. Ras genes are frequently mutated in tumours. Ras genes encode guanosine triphosphate (GTP) binding proteins which are believed to be involved in signal transduction, proliferation and malignant transformation. H-, K- and N-ras genes have been identified as mutant forms of ras (Barbacid M, Ann. Rev. Biochem. 1987, 56: 779–827). Post translational modification of ras protein is required for biological activity. Farnesylation of ras catalysed by FPTase is believed to be an essential step in ras processing. It occurs by transfer of the farnesyl group of farnesyl pyrophosphate (FPP) to a cysteine at the C-terminal tetrapeptide of ras in a structural motif called the CAAX box. After further post-translational modifications, including proteolytic cleavage at the cysteine residue of the CAAX box and methylation of the cysteine carboxyl, ras is able to attach to the cell membrane for relay of growth signals to the cell interior. In normal cells activated ras is believed to act in conjunction with growth factors to stimulate cell growth. In tumour cells it is believed that mutations in ras cause it to stimulate cell division even in the absence of growth factors (Travis J, Science 1993, 260: 1877–1878), possibly through being permanently in GTP activated form rather than cycled back to GDP inactivated form. Inhibition of farnesylation of mutant ras gene products will stop or reduce activation.

One class of known inhibitors of farnesyl transferase is based on farnesyl pyrophosphate analogues; see for example European patent application EP 534546 from Merck. Inhibitors of farnesyl transferase based on mimicry of the CAAX box have been reported Reiss (1990) in Cell β 81–8 disclosed tetrapeptides such as CVIM (Cys-Val-Ile-Met). James (1993) in Science 260, 1937–1942 disclosed benzodiazepine based peptidomimetic compounds. Lerner (1995) in J. Biol. Chem. 270, 26802 and Eisai in International Patent Application WO 95/25086 disclosed further peptidomimetic compounds based on Cys as the first residue. Bristol-Myers Squibb in European Patent Application EP 696593 disclosed for the first time farnesyl transferase inhibitors having a 4-sulfanylpyrrolidine residue in the first position. It is believed that there has been no disclosure of such compounds having a 3-sulfanyl pyrrolidine moiety in the first position.

According to one aspect of the present invention there is provided an inhibitor of ras farnesylation of Formula I

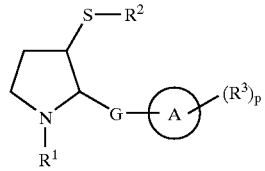

wherein:
$R^1$ is selected from H; —$C_{1-4}$alkyl; —CO—$C_{1-4}$alkyl; —CO—O—$C_{1-4}$alkyl; —CO—O—$C_{2-4}$alkenyl; —$C_{1-4}$alkylene-CONR$^4$R$^5$ (wherein $R^4$ and $R^5$ are independently selected from H and $C_{1-4}$alkyl); —$C_{1-4}$alkylene-COOR$^6$ (wherein $R^6$ is selected from H and $C_{1-4}$alkyl); —$C_{1-3}$alkylene-Ph and —CO—O(CH$_2$)$_n$Ph wherein the phenyl groups in —$C_{1-3}$alkylene-Ph and —CO—O(CH$_2$)$_n$Ph are optionally substituted by $R^a$ and/or $R^b$ and $R^a$ and $R^b$ are independently selected from $C_{1-4}$alkyl, halogen, hydroxy, $C_{1-4}$alkoxy, $C_{1-4}$alkanoyl, $C_{1-4}$alkanoyloxy, amino, $C_{1-4}$alkylamino, di($C_{1-4}$alkyl)amino, $C_{1-4}$alkanoylamino, nitro, cyano, carboxy, carbamoyl, $C_{1-4}$alkoxycarbonyl, thiol, $C_{1-4}$alkylsulfanyl, $C_{1-4}$alkylsulfinyl, $C_{1-4}$alkylsulfonyl and sulfonamido; and n=0–4;

$R^2$ is selected from H; —$C_{1-4}$alkyl; —$COC_{1-4}$alkyl; and —$COOC_{1-4}$alkyl; and —$C_{1-3}$alkylene-Ph optionally substituted on the phenyl ring by $R^a$ and/or $R^b$;

$R^3$ is selected from H; OH; CN; CF$_3$; NO$_2$; —$C_{1-4}$ alkyl; —$C_{1-4}$alkylene-$R^7$; —$C_{2-4}$alkenylene-$R^7$; —$C_{2-4}$alkynylene-$R^7$; $R^7$; OR$^7$ (where $R^7$ is selected from phenyl, naphthyl, a 5–10 membered monocyclic or bicyclic heteroaryl ring containing up to 5 heteroatoms selected from O, N and S and any aryl ring in $R^7$ is optionally substituted by $R^a$ and/or $R^b$); $C_{2-4}$alkenyl; halogen; —(CH$_2$)$_y$COOR$^8$ (where y=0–3 and $R^8$ represents H, $C_{1-4}$alkyl, or $C_{2-4}$alkenyl); —CONR$^9$R$^{10}$ (where $R^9$ and $R_{10}$ independently represent H, $C_{1-4}$alkyl, $C_{2-4}$alkenyl, —O—$C_{1-4}$alkyl, —O—$C_{2-4}$alkenyl or —$C_{1-3}$ alkylenePh (wherein Ph is optionally substituted by $R^a$ and $R^b$ as hereinabove defined); —CON(R$^{11}$)OR$^{12}$ (where $R^{11}$ and $R^{12}$ independently represent H, $C_{1-4}$alkyl or $C_{2-4}$alkenyl);

a group of Formula II: —CONR$^{13}$—CR$^{13a}$R$^{14}$—COOR$^{17}$, (where $R^{13}$ and $R^{13a}$ are independently H or $C_{1-4}$alkyl, $R^{17}$ is H or $C_{1-6}$alkyl, $R^{14}$ is selected from the side chain of a lipophilic amino acid, carbamoyl$C_{1-4}$alkyl, N-(monoC$_{1-4}$alkyl)carbamoyl$C_{1-4}$alkyl and N-(diC$_{1-4}$alkyl)carbamoyl$C_{1-4}$alkyl, the group of Formula II having L or D configuration at the chiral alpha carbon in the corresponding free amino acid; a lactone of formula:

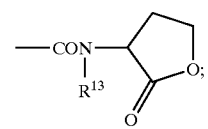

$C_{1-4}$alkyl monosubstituted on carbon with =N—OH;
a group of Formula —X—R$^{15}$ (where X is selected from O, CO, CH$_2$, S, SO, SO$_2$ and $R^{15}$ is selected from $C_{1-6}$alkyl, phenyl, naphthyl, a 5–10 membered monocyclic or bicyclic heteroaryl ring containing up to 5 heteroatoms selected from O, N and S and any aryl ring in $R^{15}$ is optionally substituted by $R^a$ and/or $R^b$;

p is 0–3 in which $R^3$ values can be the same or different;
G is a linking moiety selected from the following groups written from left to right in Formula I:

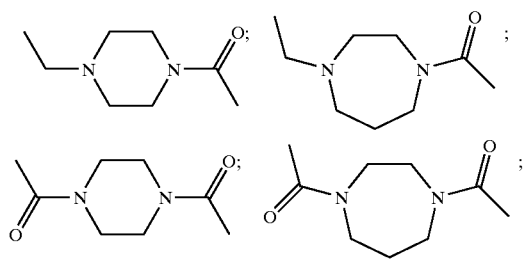

(wherein the piperazine and perhydro-1,4-diazepine rings are optionally substituted); —CO—NR$^{16}$—; —CH$_2$—NR$^{16}$—; —CH$_2$S—; —CH$_2$O—; —CH$_2$—CHR$^{16}$; —CH=CR$^{16}$—; —CH$_2$NR$^{16}$-T-; —CH$_2$NR$^{16}$—SO$_2$—; —CH$_2$—NR$^{16}$—CO-T$^1$-; —CO—NR$^{16}$-T-; —CH$_2$S-T-; —CH$_2$O-T- (where R$^{16}$ is selected from H, C$_{1-4}$alkyl, C$_{1-4}$alkylene-Z, —CO—C$_{1-4}$alkylene-Z, —CO—C$_{1-6}$alkyl, —COZ, Z and Z is selected from —O—C$_{1-4}$alkyl, phenyl, naphthyl, a 5–10 membered monocyclic or bicyclic heteroaryl ring containing up to 5 heteroatoms selected from O, N and S and any aryl ring in R$^{16}$ is optionally substituted by R$^a$ and/or R$^b$ as hereinabove defined;

where, T represents —(CH$_2$)$_m$— where m is 1–4 and T is optionally monosubstituted with any value of R$^{16}$ other than H; and where T$^1$ represents —(CH$_2$)$_{m^1}$— wherein m$^1$ is 0–4 and T$^1$ is optionally monosubstituted with any value of R$^{16}$ other than H);

A is selected from phenyl; naphthyl; a 5–10 membered monocyclic or bicyclic heteroaryl ring containing up to 5 heteroatoms where the heteroatoms are independently selected from O, N & S;

or a —S—S— dimer thereof when R$^2$=H; or a N-oxide thereof;

or a pharmaceutically acceptable salt, prodrug or solvate thereof.

In another aspect of the invention there is provided an inhibitor of ras farnesylation of Formula I
wherein:

R$^1$ is selected from H; —C$_{1-4}$alkyl; —C$_{1-3}$alkylene-Ph optionally mono or di-substituted on Ph with substituents selected from C$_{1-4}$alkyl, halogen, OH, C$_{1-4}$alkoxy, C$_{1-4}$alkanoyl, C$_{1-4}$alkanoyloxy, amino, C$_{1-4}$alkylamino, di(C$_{1-4}$alkyl)amino, C$_{1-4}$alkanoylamino, nitro, cyano, carboxy, carbamoyl, C$_{1-4}$alkoxycarbonyl, thiol, C$_{1-4}$alkylsulfanyl, C$_{1-4}$alkylsulfinyl, C$_{1-4}$alkylsulfonyl and sulfonamido; —CO—C$_{1-4}$alkyl; —CO—O—C$_{1-4}$alkyl; —CO—O—C$_{2-4}$alkenyl; —CO—O—(CH$_2$)$_n$Ph optionally substituted on Ph as defined for substitution on Ph in R$^1$=—C$_{1-3}$alkylene-Ph above and n=0–4; —C$_{1-4}$alkylene-CONR$^4$R$^5$ where R$^4$ & R$^5$ are independently selected from H and C$_{1-4}$alkyl; and —C$_{1-4}$alkylene-COOR$^6$ where R$^6$ is selected from H, C$_{1-4}$alkyl;

R$^2$ is selected from H; —C$_{1-4}$alkyl; —C$_{1-3}$alkylene-Ph optionally substituted on Ph as defined for substitution on Ph in R$^1$=—C$_{1-3}$alkylene-Ph above; —COC$_{1-4}$alkyl; and —COOC$_{1-4}$alkyl;

R$^3$ is selected from H; OH; CN; CF$_3$; NO$_2$; —C$_{1-4}$ alkyl; —C$_{1-4}$alkylene-R$^7$ where R$^7$ is selected from phenyl, naphthyl, a 5–10 membered monocyclic or bicyclic heteroaryl ring containing up to 5 heteroatoms selected from O, N and S and any aryl ring in R$^7$ is optionally substituted as defined for substitution on the Ph group in R$^1$=—C$_{1-3}$alkylene-Ph above; R$^7$; C$_{2-4}$alkenyl; halogen;

—(CH$_2$)$_y$COOR$^8$ where y=0–3 and R$^8$ represents H, C$_{1-4}$alkyl, or C$_{2-4}$alkenyl; —CONR$^9$R$^{10}$ where R$^9$ and R$^{10}$ independently represent H, C$_{1-4}$alkyl, C$_{2-4}$alkenyl, —O—C$_{1-4}$alkyl, —O—C$_{2-4}$alkenyl, —C$_{1-3}$alkylenePh optionally substituted as defined for this group for R$^1$ above; —CON(R$^{11}$)OR$^{12}$ where R$^{11}$ and R$^{12}$ independently represent H, C$_{1-4}$alkyl and C$_{2-4}$alkenyl;

a group of Formula II, —CONR$^{13}$—CHR$^{14}$—COOR$^{17}$, where R$^{13}$ is H or C$_{1-4}$alkyl, R$^{17}$ is H or C$_{1-6}$alkyl, R$^{14}$ is selected from the side chain of a lipophilic amino acid, carbamoylC$_{1-4}$alkyl, N-(monoC$_{1-4}$alkyl)carbamoylC$_{1-4}$alkyl and N-(diC$_{1-4}$alkyl)carbamoylC$_{1-4}$alkyl, the group of Formula II having L or D configuration at the chiral alpha carbon in the corresponding free amino acid; a lactone of formula

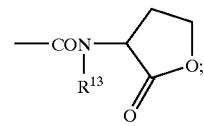

C$_{1-4}$alkyl monosubstituted on carbon with =N—OH;

a group of Formula —X—R$^{15}$ where X is selected from O, CO, CH$_2$, S, SO, SO$_2$ and R$^{15}$ is selected from C$_{1-6}$alkyl, phenyl, naphthyl, a 5–10 membered monocyclic or bicyclic heteroaryl ring containing up to 5 heteroatoms selected from O, N and S and any aryl ring in R$^{15}$ is optionally substituted as defined for the Ph group in R$^1$=—C$_{1-3}$alkylene-Ph;

p is 0–3 in which R$^3$ values can be the same or different;

G is a linking moiety selected from the following groups written from left to right in Formula I:

—CO—NR$^{16}$— where R$^{16}$ is selected from H, C$_{1-4}$alkyl, C$_{1-4}$alkylene-Z, —CO—C$_{1-4}$alkylene-Z, —CO—C$_{1-6}$alkyl, —COZ, Z and Z is selected from —O—C$_{1-4}$alkyl, phenyl, naphthyl, a 5–10 membered monocyclic or bicyclic heteroaryl ring containing up to 5 heteroatoms selected from O, N and S and any aryl ring in R$^{16}$ is optionally substituted as defined for the Ph group in R$^1$=—C$_{1-3}$alkylene-Ph; —CH$_2$—NR$^{18}$— where R$^{18}$ represents any value defined for R$^{16}$; —CH$_2$S—; —CH$_2$O—; —CH$_2$—CHR$^{19}$— where R$^{19}$ represents any value defined for R$^{16}$; —CH=CR$^{20}$— where R$^{20}$ represents any value defined for R$^{16}$; —CH$_2$NR$^{21}$-T- where R$^{21}$ represents any value defined for R$^{16}$, T represents —(CH$_2$)$_w$— where w is 1–4 and T is optionally monosubstituted with R$^{22}$ where R$^{22}$ represents any value for R$^{16}$ other than H; —CH$_2$NR$^{23}$—SO$_2$— where R$^{23}$ represents any value defined for R$^{16}$; —CH$_2$—NR$^{24}$—CO-T$^1$- where R$^{24}$ represents any value defined for R$^{16}$, T$^1$ represents) —(CH$_2$)$_{w^1}$— where w$^1$ is 0–4 and T$^1$ is optionally monosubstituted with R$^{29}$ where R$^{29}$ represents any value for R$^{16}$ other than H; —CO—NR$^{25}$-T- where R$^{25}$ represents any value defined for R$^{16}$, T represents —(CH$_2$)$_w$— where w is 1–4 and T is optionally monosubstituted with R$^{26}$ where R$^{26}$ represents any value for R$^{16}$ other than H; —CH$_2$S-T- where T represents —(CH$_2$)$_w$— where w is 1–4 and T is optionally monosubstituted with R$^{27}$ where R$^{27}$ represents any value for R$^{16}$ other than H; —CH$_2$O-T- where T represents —(CH$_2$)$_w$— where w is 1–4 and T is optionally monosubstituted with R$^{28}$ where R$^{28}$ represents any value for R$^{16}$ other than H;

A is selected from phenyl; naphthyl; a 5–10 membered monocyclic or bicyclic heteroaryl ring containing up to 5 heteroatoms where the heteroatoms are independently selected from O, N & S;

or a —S—S— dimer thereof when R²=H; or a N-oxide thereof;

or an enantiomer, diastereoisomer, pharmaceutically acceptable salt, prodrug or solvate thereof.

In another aspect of the invention the group of Formula II is expanded to allow substitution of H by $C_{1-4}$alkyl at the α carbon (to which $R^{14}$ is attached) such that Formula II becomes —CONR¹³—CR¹³ᵃR¹⁴—COOR¹⁷ where $R^{13a}$ represents H or $C_{1-4}$alkyl and other variable groups take any of the values (ranging from general to specific within the scope of Formula I) described herein.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms The term "halogen" refers to fluorine, chlorine, bromine and iodine. The term "carbamoyl" refers to —C(O)NH₂. The term "BOC" refers to tert-butyl-O—C(O)—. The term "allyl" refers to CH₂=CH—CH₂—. Bicyclic aryl and bicyclic heteroaryl rings refer to ring systems in which both rings of the bicyclic system are aromatic.

Examples of $C_{1-6}$alkyl include methyl, ethyl, propyl, isopropyl, sec-butyl, tert-butyl and pentyl; examples of $C_{1-4}$alkyl include methyl, ethyl, propyl, isopropyl, sec-butyl and tert-butyl; examples of $C_{1-3}$alkyl include methyl, ethyl, propyl and isopropyl; examples of —$C_{1-3}$alkylenePh include benzyl, phenylethyl, phenylpropyl; examples of $C_{1-4}$alkoxy (also called —O—$C_{1-4}$alkyl herein) include methoxy, ethoxy and propoxy; examples of $C_{1-4}$alkanoyl include formyl, acetyl and propionyl; examples of $C_{1-4}$alkanoyloxy include acetyloxy and propionyloxy; examples of $C_{1-4}$alkylamino include methylamino, ethylamino, propylamino, isopropylamino, sec-butylamino and tert-butylamino; examples of di-($C_{1-4}$alkyl)amino include di-methylamino, di-ethylamino and N-ethyl-N-methylamino; examples of $C_{1-4}$alkanylamin include acetamido and propionylamino; examples of $C_{1-4}$alkoxycarbonyl include methoxycarbonyl, ethoxycarbonyl and propoxycarbonyl; examples of $C_{1-4}$alkylsulfanyl include methylsulfanyl, ethylsulfanyl, propylsulfanyl, isopropylsulfanyl, sec-butylsulfanyl and tert-butylsulfanyl; examples of $C_{1-4}$alkylsulfinyl include methylsulfinyl, ethylsulfinyl, propylsulfinyl, isopropylsulfinyl, sec-butylsulfmyl and tert-butylsulfmyl; examples of $C_{1-4}$alkylsulfonyl include methylsulfonyl, ethylsulfonyl, propylsulfonyl, isopropylsulfonyl, sec-butylsulfonyl and tert-butylsulfonyl; examples of —CO—$C_{1-4}$alkyl include formyl, acetyl, propionyl, butyryl, and valeryl; examples of —CO—O—$C_{1-4}$alkyl include ethyloxycarbonyl; propyloxycarbonyl and tert-butyloxycarbonyl (BOC); examples of —CO—O—$C_{2-4}$alkenyl include allyloxycarbonyl and vinyloxycarbonyl; examples of —CO—O—(CH2)$_n$Ph where n=0–4 include phenyloxycarbonyl, benzyloxycarbonyl, phenylethyloxycarbonyl and phenylpropyloxycarbonyl; examples of —$C_{1-4}$alkylene-CONR⁴R⁵ include carbamoylmethyl, carbamoylethyl, N-methylcarbamoylethyl, N-methyl-N-ethylcarbamoylethyl; examples of —$C_{1-4}$alkylene-COOR⁶ include carboxymethyl, carboxyethyl, carboxypropyl, propionic acid methyl ester, acetic acid ethyl ester; examples of $C_{2-4}$alkenyl include allyl and vinyl; examples of —O—$C_{2-4}$alkenyl include allyloxy and vinyloxy; examples of lipophilic amino acids include valine, leucine, isoleucine, methionine, phenylalanine, serine, threonine and tyrosine; examples of carbamoyl$C_{1-4}$alkyl include carbarmoylmethyl, carbamoylethyl and carbamoylpropyl; examples of N-(mono$C_{1-4}$alkyl)carbamoyl$C_{1-4}$alkyl include N-methylcarbamoylmethyl and N-ethyl carbamoylethyl; examples of N-(di$C_{1-4}$alkyl)carbamoyl-$C_{1-4}$alkyl include N,N-dimethylcarbamoylethyl and N-methyl-N-ethylcarbamoylethyl; examples of $C_{1-4}$alkyl monosubstituted on carbon with =N—OH include butyraldehyde oxime and propionaldehyde oxime; examples of hydroxy$C_{1-6}$alkyl include hydroxymethyl, hydroxyethyl, hydroxypropyl, 2-hydroxypropyl, 2-(hydroxymethyl)propyl and hydroxypentyl; examples of $C_{1-6}$alkoxy$C_{1-6}$alkyl include methoxyethyl, ethoxyethyl and methoxybutyl; examples of $C_{1-6}$alkylcarbonyl include methylcarbonyl, ethylcarbonyl, propylcarbonyl, isopropylcarbonyl, sec-butylcarbonyl, tert-butylcarbonyl and pentylcarbonyl; examples of hydroxy$C_{1-6}$alkylcarbonyl include hydroxyacetyl, hydroxypropionyl, hydroxybutyryl, 3-hydroxybutyryl and hydroxypentanoyl, examples of $C_{1-6}$alkoxy$C_{1-6}$alkylcarbonyl include methoxyacetyl, methoxypropionyl, ethoxybutyryl and butoxyacetyl; examples of phenyl$C_{1-6}$alkyl include benzyl, phenylethyl and phenylpropyl; examples of —CO—$C_{1-4}$alkyl-Ph include phenylacetyl and phenylpropionyl; examples of —CO—$C_{1-4}$alkyl-heteroaryl include 2-(3-pyridyl)-acetyl and 2-(3-thienyl)-acetyl; examples of N-($C_{1-6}$alkyl) carbamoyl include N-methyl-carbamoyl and N-ethyl carbamoyl; examples of N-(di$C_{1-6}$alkyl)carbamoyl include N,N-dimethylcarbamoyl and N-methyl-N-ethylcarbamoyl.

Examples of 5–10 membered monocyclic or bicyclic heteroaryl rings containing up to 5 heteroatoms selected from O, N and S include the following: Examples of 5- or 6-membered heteroaryl ring systems include imidazole, triazole, pyrazine. pyrimidine, pyridazine, pyridine, isoxazole, oxazole, isothiazole, thiazole and thiophene. A 9 or 10 membered bicyclic heteroaryl ring system is an aromatic bicyclic ring system comprising a 6-membered ring fused to either a 5 membered ring or another 6 membered ring. Examples of 5/6 and 6/6 bicyclic ring systems include benzofuran, benzimidazole, benzthiophene, benzthiazole, benzisothiazole, benzoxazole, benzisoxazole, pyridoimidazole, pyrimidoimidazole, quinoline, isoquinoline, quinoxaline, quinazoline, phthalazine, cinnoline and naphthyridine.

Preferably monocyclic heteroaryl rings contain upto 3 heteroatoms and bicyclic heteroaryl rings contain upto 5 heteroatoms. Preferred heteroatoms are N and S, especially N. In general, attachment of heterocyclic rings to other groups is via carbon atoms. Suitable values of heterocycles containing only N as the heteroatom are pyrrole, pyridine, indole, quinoline, isoquinoline, imidazole, pyrazine, pyrimidine, purine and pteridine.

The term 'lipophilic amino acid' as used in this specification encompasses both natural and unnatural amino acids.

Examples of lipophilic amino acids which contribute their side chain (denoted $R^{14}$ within the definition of values for $R^3$) include methionine, phenylglycine, phenylalanine, serine, leucine, isoleucine or valine. L configuration in the corresponding free amino acid is preferred. Examples of amino acid side chains are set out below. A preferred value for $R^{14}$ is —CH₂—CH₂—S—CH₃. Further preferred values for $R^{14}$ are —CH₂—OMe and —CH₂—CH₂—OMe. Some examples of amino acids and their side chains are given below:

Amino Acid Side Chain
methionine —CH₂—CH₂—S—CH₃
phenylglycine Ph phenylalanine —CH$_2$-Ph serine —CH$_2$OH or a C$_{1-4}$akyl (preferably methyl) ether thereof.

Leucine —CH$_2$—CHMe$_2$ homoserine —CH$_2$—CH$_2$—OH or a C$_{1-4}$alkyl (preferably methyl) ether thereof.

When R$^{17}$ is H to give a COOH group in Formula II, and R$^{14}$ is —CH$_2$—CH$_2$—OH then a lactone can be formed where R$^{17}$ and R$^{14}$ together form part of a dihydrofuran-2-one heterocyclic ring. The same lactone can be formed for compounds of Formula III hereinbelow, where X$^4$ is OH and X$^3$ is H.

Preferably R$^1$ is selected from H; —CO—O—(CH$_2$)$_n$Ph optionally substituted on phenyl hereinabove defined; —CO—O—C$_{2-4}$alkenyl; —CO—C$_{1-4}$alkyl; —C$_{1-4}$ alkylene-CONR$^4$R$^5$ where R$^4$ and R$^5$ are independently selected from H, C$_{1-4}$alkyl.

Most preferably R$^1$ is hydrogen.

Preferably R$^2$ is selected from H and —CO—C$_{1-4}$alkyl.

Most preferably R$^2$ is hydrogen.

Preferably G is selected from —CH$_2$—NR$^{16}$— and —CH$_2$NR$^{16}$-T.

Preferably A is selected from phenyl, naphthyl, pyridyl and thienyl.

Most preferably A is phenyl or naphthyl.

Preferably combinations of R$^3$ and p are selected from:
i) R$^3$ is selected from a group of Formula II, —C$_{1-4}$alkylR$^7$, —O—R$^7$ and R$^7$; and p=1–3 with the proviso that at least one of R$^3$ is a group of the Formula II;
ii) p=0 with the proviso that A is naphthyl and G is —CH$_2$NR$^{16}$-T; and
iii) p=1 with the proviso that R$^3$=a group of Formula II and A is phenyl or naphthyl.

Suitable pairs of values for R$^3$ when p=2 are: —COOMe, —CO.N(Me).OMe; NO$_2$, —CO.N(Me).OMe; —COOMe, allyloxycarbonyl; —CO.N(Me).OMe, allyloxycarbonyl; allyloxycarbonyl, —CO.N(Me).O.CH$_2$CH=CH$_2$; OH, COOH; —COOMe, COOMe; Ph, —CO.N-Methionine methyl ester, Ph, —CO.N-Methionine; benzyl, —CO.N-Methionine methyl ester, benzyl, —CO.N-Methionine; benzyl. —CO.N-Methionine isopropyl ester, Ph, —CO.Nα-Glutamine methyl ester; and Ph. —CO.Nα-Glutamine.

Suitable values for G=CH$_2$NR$^{16}$T include CH$_2$N (CO.CH$_2$.CHMe$_2$).CH$_2$.CH$_2$; CH$_2$.N(CH$_2$ CH$_2$ CH$_2$OMe). CH$_2$.CH$_2$; CH$_2$.N(CH$_2$.pPh.OMe).CH$_2$.CH$_2$; CH$_2$.N (CO.CH$_2$.CHMe$_2$).CH$_2$; CH$_2$N(CO.CH$_2$.CH$_2$.CH$_2$.Me). CH$_2$; CH$_2$N(CO.CH$_2$.CHMe.CH$_2$Me).CH$_2$; CH$_2$N (CO.CH$_2$.CH$_2$.OMe)CH$_2$; CH$_2$N(CO.CH$_2$.pyridin-3-yl) .CH$_2$; CH$_2$N(4-methoxybenzyl)CH$_2$; CH$_2$N (CO.CH$_2$.CHMe$_2$)CH$_2$.CH$_2$.CH(Ph); CH$_2$N(CO.CH$_3$) CH$_2$.CH$_2$.CH(Ph); CH$_2$N(CO.CH$_2$.CHMe$_2$)CH$_2$; CH$_2$N (CO.CH$_3$)CH$_2$; CH$_2$N(CO.CH$_2$.CHMe$_2$)CH$_2$.CH(Ph); CH$_2$N(CO.CH$_2$.CMe$_3$)CH$_2$.CH(Ph); CH$_2$N (CO.CH$_2$.pyridin-3-yl)CH$_2$.CH(Ph); CH$_2$N(CO.1-hydroxy-6-methoxy-pyridin-3-yl)CH$_2$.CH(Ph); CH$_2$N(CO.CH$_2$ pyrid-3-yl)CH$_2$CH(Ph); CH$_2$N(CO.CH$_2$CHMe$_2$)CH$_2$.CH$_2$; CH$_2$N(CO.CH$_2$CMe$_3$)CH$_2$.CH$_2$; CH$_2$N(CO thiazol-2-yl) CH$_2$CH$_2$; CH$_2$N(CO 1-oxido-6-hydroxypyridin-3-yl) CH$_2$CH$_2$; CH$_2$N(CO.CH$_2$pyridin-3-yl)CH$_2$.CH$_2$ and CH$_2$N (CO.4-methoxybenzyl)CH$_2$.CH$_2$.

Preferred values for CH$_2$NR$^{16}$T include CH$_2$N (CO.CH$_2$.CHMe$_2$)CH$_2$.CH(Ph); CH$_2$N (CO.CH$_2$ pyridin-3-yl)CH$_2$.CH(Ph); CH$_2$N(CO.1-hydroxy-6-hydroxypyridin-3-yl)CH$_2$.CH(Ph); CH$_2$N(CO thiazol-2-yl); CH$_2$.CH$_2$; and CH$_2$N (CO.1-oxido-6-hydroxypyridin-3-yl) CH$_2$.CH$_2$.

Suitable values for G=—CH$_2$NR$^{16}$ — include CH$_2$NH; CH$_2$NMe; CH$_2$N(CO.CH$_2$.CHMe$_2$) and CH$_2$N (CO.CH$_2$.CH$_2$.OMe). A preferred value for —CH$_2$NR$^{16}$— is —CH$_2$NH—.

When G is —CH$_2$NR$^{16}$-T- a suitable value for m is 1. When G is —CH$_2$—NR$^{16}$—CO-T$^1$- a suitable value for m$^1$ is 1. When G is —CH$_2$—NR$^{16}$-T- a suitable value for m is 1. When G is —CH$_2$—S-T- a suitable value for m is 1. When G is —CH$_2$—O-T- a suitable value for m is 1.

G is especially —CONH—, —CH$_2$.NH—, —CH$_2$NHSO$_2$—, —CH$_2$NHCO—.

In another aspect G is of the formula

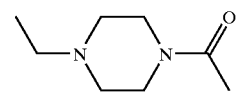

wherein the piperazine ring is optionally substituted by C$_{1-4}$alkoxyC$_{1-4}$alkyl, phenoxyC$_{1-4}$alkyl or heteroaryloxyC$_{1-4}$ alkyl.

Preferably, when G is of the formula

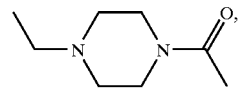

A is naphthyl.

Preferred compounds of the invention are any of the formulae III, IV and V:

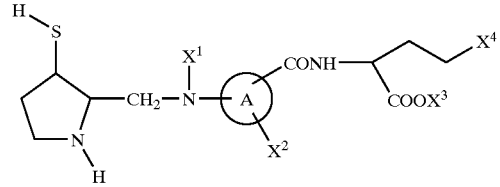

Formula III wherein:

X$^1$ is selected from H; C$_{1-6}$alkyl; hydroxyC$_{1-6}$alkyl, C$_{1-6}$alkoxyC$_{1-6}$alkyl; C$_{1-6}$alkylcarbonyl; hydroxyC$_{1-6}$ alkylcarbonyl; C$_{1-6}$alkoxyC$_{1-6}$alkylcarbonyl;

A is selected from phenyl, naphthyl or a 5–10 membered heterocyclic ring having upto 5 heteroatoms selected from O, N and S;

X$^2$ is selected from H; phenyl; phenylC$_{1-6}$alkyl; a 5–6 membered heteroaryl ring containing up to 3 heteroatoms selected from O, N and S optionally linked to A by C$_{1-6}$alkyl; and X$^2$ is optionally substituted on any ring by R$^a$ and/or R$^b$ as hereinabove defined;

X$^3$ is selected from H; C$_{1-6}$alkyl;

X$^4$ is selected from C$_{1-6}$alkylsulfanyl; C$_{1-6}$alkylsulfinyl; C$_{1-6}$alkylsulfonyl; carbamoyl; N-(C$_{1-6}$alkyl)carbamoyl; N-diC$_{1-6}$alkyl)carbamoyl; and hydroxy or a C$_{1-4}$alkyl ether thereof;

Formula IV

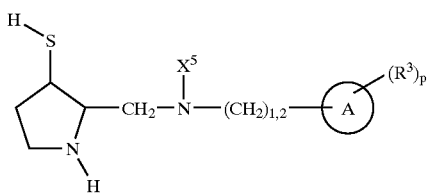

wherein:
X⁵ is selected from $C_{1-4}$alkyloxy$C_{1-4}$alkyl; —$C_{1-4}$alkylPh; —CO—$C_{1-4}$alkyl-Ph; —CO—$C_{1-6}$alkyl; —CO—$C_{1-4}$alkyl-heteroaryl where heteroaryl is a 5–10 membered heteroaryl ring containing up to 5 heteroatoms selected from O, N and S and Ph or heteroaryl are optionally substituted by $R^a$ and/or $R^b$ as hereinabove defined; $C_{1-4}$alkyloxy$C_{1-4}$alkyl;
A is naphthyl or a 10 membered heteroaryl ring having upto 5 heteroatoms selected from O, N and S;
$R^3$ and p are as defined above;

Formula V

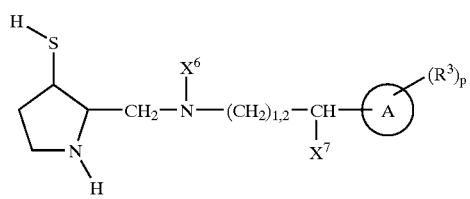

wherein:
$X^6$ has any value defined for $X^5$ in ii) above;
$X^7$ is Ph optionally substituted by $R^a$ and/or $R^b$ as hereinabove defined;
A is Ph or naphthyl or a 5–10 membered heteroaryl ring having upto 5 heteroatoms selected from O, N and S:
$R^3$ and p are as defined above;
or a N-oxide, pharmaceutically acceptable salt, prodrug or solvate thereof.

A preferred values for compounds of the formula III include,
$X^1$ is selected from H and $C_{1-6}$alkoxy$C_{1-6}$alkyl;
$X^2$ is selected from H; phenyl and phenyl$C_{1-6}$alkyl;
$X_4$ is $C_{1-6}$alkylsulfanyl; and
A is selected from phenyl and naphthyl.
Other preferred values for $X^4$ are —OMe and the lactone which can be formed when $X^4$ is OH and $X^3$ is H.

A preferred value for compounds of the formula IV is p is 0.

Preferred values for compounds of the formula V include:
$X^7$ is phenyl;
A is phenyl; and
p is 0.

In another embodiment of the invention preferred values are set out below:

In compounds of Formula III: $X^1$ is H or methoxy$C_{1-4}$alkyl (especially H); $X^2$ is H, phenyl, benzyl, phenethyl, 4-methylphenethyl or 4-methylphenylacetylene (especially benzyl); $X^3$ is H or $C_{1-4}$alkyl (especially H); $X^4$ is $C_{1-4}$alkylsulfanyl (especially methylsulfanyl); and A is phenyl. When A is a 6-membered aryl or heteroaryl ring then groups —NX¹— and the substituent comprising $X^4$ are preferably in meta juxtaposition relative to each other; and $X^2$, if present, is preferably positioned para relative to —NX¹—. The chiral carbon to which —COOX³ is attached is preferably in S configuration. The chiral carbons at the 2 and 3 positions of the pyrrolidine ring are preferably in R configuration.

In compounds of Formula IV: $X^5$ is pyridylmethylcarbonyl, thiazolylcarbonyl, 1-oxoidopyridylcarbonyl, —CO—$C_{1-4}$alkyl (especially —CO—CH₂—CHMe₂) or —CH₂-Ph-O—$C_{1-4}$alkyl (especially —CH₂-Ph-OMe); and A is phenyl or naphthyl and p is 0. The chiral carbons at the 2 and 3 positions of the pyrrolidine ring are preferably in R configuration. The attachment point for A relative to —(CH₂)$_{1,2}$— is preferably at the 1 position of napththalene and the equivalent position for heterocyclic values for A (regardless of ring numbering conventions for heterocycles). A preferred value for —(CH₂)$_{1,2}$— is —(CH₂)₂—.

In compounds of Formula V: $X^6$ is pyridylmethylcarbonyl, thiazozolylcarbonyl, 1-oxidopyridylcarbonyl, —CO—$C_{1-5}$alkyl (more preferably —CO—CH₂—CHMe₂ or —CO—CH₂-t-butyl, especially —CO—CH₂—CHMe₂) or —CH₂-Ph-O—$C_{1-4}$alkyl (especially —CH₂-Ph-OMe); $X^7$ is phenyl; and A is phenyl or naphthyl (especially phenyl) and p is 0. The chiral carbons at the 2 and 3 positions of the pyrrolidine ring are preferably in R configuration. A preferred value for —(CH₂)$_{1,2}$— is —CH₂—.

It is to be understood that, insofar as certain of the compounds of Formula I defined above may exist in optically active or racemic forms by virtue of one or more asymmetric carbon atoms, the invention includes in its definition any such optically active or racemic form which possesses the property of inhibiting FTPase. The synthesis of optically active forms may be carried out by standard techniques of organic chemistry well known in the art, for example by synthesis from optically active starting materials or by resolution of a racemic form. Similarly, inhibitory properties against FTPase may be evaluated using the standard laboratory techniques referred to hereinafter.

Preferably substituents on the 2 and 3 positions of the pyrrolidine ring in compounds of the Formula I are in the cis configuration.

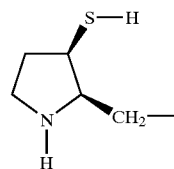

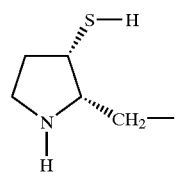

Another suitable configuration is the trans configuration.

According to another aspect of the present invention there is provided any one of the following individual compounds or a pharmaceutically acceptable salt thereof:

(2S)-2-{2-benzyl-5-[(cis)-3-sulfanylpyrrolidin-2-ylmethyl amino]-benzoylamino}-4-methylsulfanylbutyric acid methyl ester;

(2S)-2-{2-benzyl-5-[(cis)-3-sulfanylpyrrolidin-2-ylmethyl amino]-benzoylamino}-4-methylsulfanylbutyric acid;

(2S)-2-({2-phenyl-5-[(cis)-3-sulfanylpyrrolidin-2-ylmethyl amino]-phenylcarbonyl}amino)-4-methylsulfanylbutyric acid methyl ester;

(2S)-2-({2-phenyl-5-[(cis)-3-sulfanylpyrrolidin-2-ylmethyl amino]-phenylcarbonyl}-amino)-4-methylsulfanylbutyric acid;

(2S)-2-[(cis)-3-sulfanylpyrrolidin-2-ylmethyl)amino]-naphthalene-1-carbonyl}-amino)-4-methylsulfanylbutyric acid methyl ester;

(2S)-2-({3-[(cis)-3-sulfanylpyrrolidin-2-ylmethyl)amino]-naphthalene-1-carbonyl}-amino)-4-methylsulfanylbutyric acid;

(2S)-2-({-3-phenyl-5[(cis)-3-sulfanylpyrrolidin-2-ylmethyl amino]-phenylcarbonyl}-amino)-4-methylsulfanylbutyric acid methyl ester;

(2S)-2-({-3-phenyl-5[(cis)-3-sulfanylpyrrolidin-2-ylmethyl amino]-phenylcarbonyl}amino)-4-methylsulfanylbutyric acid;

(cis)-2-[{N-(4-methoxybenzyl)-N-naphthalen-1-ylmethylamino}-methyl]-pyrrolidine-3-thiol;

N-(naphthalen-1-ylmethyl)-N-[(cis)-3-sulfanylpyrrolidin-2-ylmethyl)-pentanamide;

N-naphthalen-1-ylmethyl)-N-[(cis)-3-sulfanylpyrrolidin-2-ylmethyl)-2-(pyridin-3-yl)-acetamide;

N-[(cis)-3-sulfanyl-pyrrolidin-2-ylmethyl)-3-methyl-N-(2-naphthalen-1-yl-ethyl)butyramide;

N-[(cis)-3-sulfanyl-pyrrolidin-2-ylmethyl)-N-(2-naphthalen-1-yl-ethyl)-2-pyridin-3-yl-acetamide;

(cis)-2-{[(3-methoxypropyl)-(2-naphthalen-1-ylethyl)amino]methyl}-pyrrolidine-3-thiol;

N-[(cis)-3-sulfanyl-pyrrolidin-2-ylmethyl)-2-(4methoxy-phenyl)-N-(2-naphthalen-2-yl-ethyl)-acetamide;

(cis)-2-{[(2-(4-methoxyphenyl)ethyl)-(2-naphthalen-1-ylethyl)amino]methyl}-pyrrolidine-3-thiol;

N-(2,2-diphenyl-ethyl)-N-[(cis)-3-sulfanyl-pyrrolidin-2-ylmethyl)-3-methyl-butyramide;

N-[(cis)-3-sulfanyl-pyrrolidin-2-ylmethyl)-3,3-dimethyl-N-(2-naphthalen-2-yl-ethyl)-butyramide;

N-2,2-diphenyl-ethyl)-N-[(cis)-3-sulfanyl-pyrrolidin-2-ylmethyl)-3,3-dimethyl-butyramide;

(2S)-2-{3-[(cis)-3-sulfanyl-pyrrolidin-2-ylmethyl)-(3-methoxy-propyl)amino]-benzoylamino}-4-methylsulfanyl-butyric acid;

N-[(cis)-3-sulfanyl-pyrrolidin-2-ylmethyl)-3,3-dimethyl-N-(2-naphthalen-1-yl-ethyl)-butyramide;

(2S)-4-carbamoyl-2-({2-phenyl-5-[(cis)-3-sulfanyl-pyrrolidin-2-ylmethyl)-amino]-phenylcarbonyl}-amino)-butyric acid;

(2S)-4-carbamoyl-2-({2-phenyl-5-[(cis)-3-sulfanyl-pyrrolidin-2-ylmethyl)-amino]-phenylcarbonyl}-amino)-butyric acid methyl ester, 2-(3-pyridyl)-N-(2,2-diphenyl-ethyl)-N-(cis)-3-sulfanylpyrrolidin-2-ylmethyl)-acetamide;

6-methoxy-1-oxido-N-(2,2-diphenyl-ethyl)-N-(cis)-3-sulfanylpyrrolidin-2-ylmethyl)-pyridine-3-carboxamide;

N-(naphthyl-1-yl-ethyl)-N-[(cis)-3-sulfanylpyrrolidin-2yl-methyl)-thiazole-5-carboxamide;

6-methoxy-1-oxido-N-(naphthyl-1-yl-ethyl)-N-(cis)-3-sulfanylpyrrolidin-2-ylmethyl)-pyridine-3-carboxamide;

(2S)-2-{2-benzyl-4-[(cis)-3-sulfanyl-pyrrolidin-2-ylmethyl)-amino]-benzoylamino}-4-methylsulfanyl-butyric acid;

(2S)-2-(2-methoxy-ethyl)-1-[(cis)-3-sulfanyl-pyrrolidin-2-ylmethyl)-4-naphthoyl-piperazine; and (2S)-2-{2-benzyl-5-[(cis)-3-sulfanylpyrrolidin-2-ylmethy)amino]-benzoylamino}-4-methylsulfanylbutyric acid;

(2S)-2-{2-benzyl-4-[(cis-3-sulfanylpyrrolidin-2-ylmethyl)amino]-benzoylamino}-4-methylsulfanylbutyric acid;

(2S)-2-{2-phenethyl-5-[(trans)-3-sulfanylpyrrolidin-2-ylmethylamino]benzoylamino}-4-methylsulfanyl butyric acid;

(2S)-2-{phenethyl-5-[(cis)-3-sulfanylpyrrolidin-2-ylmethylamino]-benzoylamino}-4-methylsulfanyl butyric acid;

(2S)-2-{2-benzyl-5-[(trans)-3-sulfanylpyrrolidin-2-ylmethyl amino]-benzoylamino}-4-methylsulfanylbutyric acid;

(2S)-2-{2-(phenethyl-5-[(cis)-3-sulfanylpyrrolidin-2-yl methylamino]-benzoylamino}-4-methylsulfanylbutyric acid;

(2S)-2-{2-(4-methylphenylethynyl)-4-[(cis)-3-sulfany lpyrrolidin-2-ylmethylamino]-benzoylamino}-4-methylsulfanyibutyric acid;

(2S)-2-{2-benzyl-5-[(cis)-3-sulfanylpyrrolidin-2-ylmethyl amino]-benzoylamino}-4-methylsulfanylbutyric acid isopropyl ester, (2S)-2-{2-benzyl-4-(cis-3-sulfanylpyrrolidin-2-ylmethyl amino]-benzoylamino}-4-methylsulfanylbutyric acid methyl ester;

(2S)-2-{2-benzyl-4-[(trans)-3-sulfanylpyrrolidin-2-ylmethyl amino]-benzoylamino}-4-methylsulfanylbutyric acid methyl ester, (2S)-2-{2-benzyl-5-[(trans)-3-sulfanylpyrrolidin-2-ylmethyl amino]-benzoylamino}-4-methylsulfanylbutyric acid methyl ester, (2S)-2-{2-phenyl-5-[(trans)-3-sulfanylpyrrolidin-2-ylmethyl amino]-benzoylamino}-4-methylsulfanylbutyric acid methyl ester;

(2S)-2-{2-phenyl-5-[(cis)-3-sulfanylpyrrolidin-2-ylmethyl amino]-benzoylamino}-4-methylsulfanylbutyric acid methyl ester;

(2S)-2-{2-benzyl-5-[(cis)-3-sulfanylpyrrolidin-2-ylmethyl amino]-benzoylamino}-4-methylsulfanylbutyric acid methyl ester, ( (2S)-2-{2-(4-methylphenethyl)-4-[(cis)-3-sulfanyl pyrrolidin-2-ylmethylamino]-benzoylamino}-4-methylsulfanylbutyric acid methyl ester;
(2S)-2-{2-(4-methylphenylethynyl)-4-[(cis)-3-sulfanyl pyrrolidin-2-ylmethyl)amino]-benzoylamino}-4-methylsulfanylbutyric acid methyl ester;
(2S)-2-(2-methoxyethyl)-1-[(cis)-3-sulfanylpyrrolidin-2-ylmethyl]-4-(naphth-1-oyl)piperazine;
(cis)-2-[N-isovaleryl-N-(2-(naphth-1-yl)ethyl)aminiomethyl]-3-sulfanylpyrrolidine;
(cis)-2-[N-(3-pyridylacetyl)-N-(naphth-1-yl)ethyl)aminomethyl]-3-sulfanylpyrrolidine;
(cis)-2-[N-(1-oxido-6-mlethoxypyridin-3-ylcarbonyl;
(cis)-2-[N-(thiazol-5-ylcarbonyl) N-(naphth-1-yl)ethyl)aminomethyl]-3-sulfanylpyrrolidine;
(2S)-2-[2-(4-fluorophenethyl)-4-[(cis)-3-sulfanyl)-pyrrolidin-2-ylmethylamino)benzoylamino]-4-methylsulfanylbutyric acid;
methyl (2S)-2-[2-(4-fluorophenethyl)-4-[(cis)-3-sulfanylpyrrolidin-2-ylmethylamino)benzoylamino]-4-methylsulfanylbutyrate; and
(2S)-2-[2-(4-fluorophenethyl)-5-((2R,3R)-3-sulfanyl-pyrrolidin-2-ylmethylamino)benzoylamino] 4methylsulfanylbutyric acid.

According to yet another aspect of the present invention there is provided any one of the following individual compounds or a pharmaceutically acceptable salt thereof:
(2S)-2-{2-Benzyl-5-[([2R,3R]-3-sulfanylpyrrolidin-2-ylmethyl)-amino)-benzoylamino}-4-methylsulfanylbutyric acid methyl ester;
(2S)-2-{2-Benzyl-5-[([2R,3R]-3-sulfanylpyrrolidin-2-ylmethyl)-amino]-benzoylamino}-4-methylsulfanylbutyric acid;
(2S)-2-({2-phenyl-5-[([2R,3R]-3-sulfanylpyrrolidin-2-ylmethyl)amino]-phenyl carbonyl}-amino)-4-methylsulfanylbutyric acid methyl ester;
(2S)-2-({2-phenyl-5-[([2R,3R]-3-sulfanylpyrrolidin-2-ylmethyl)-amino}-phenylcarbonyl}-amino)-4-methylsulfanylbutyric acid;
(2S)-2-({3-[([2R,3R]-3-sulfanylpyrrolidin-2-ylmethyl)-amino]-naphthalene-1-carbonyl}-amino)-4-methylsulfanylbutyric acid methyl ester;
(2S)-2-({3-[([2R,3R]-3-sulfanylpyrrolidin-2-ylmethyl)-amino]-naphthalene-1-carbonyl}-amino)-4-methylsulfanylbutyric acid;
(2S)-2-({-3-phenyl-5[([2R,3R]-3-sulfanylpyrrolidin-2-ylmethyl)-amino]-phenylcarbonyl}-amino)-4-methylsulfanylbutyric acid methyl ester;
(2S)-2-({-3-phenyl-5[([2R,3R]-3-sulfanylpyrrolidin-2-ylmethyl)amino]-phenylcarbonyl}-amino)-4-methylsulfanylbutyric acid;
(2R,3R)-2-[{N-(4-methoxybenzyl)-N-(naphthalen-1-ylmethyl)-amino}-methyl]-pyrrolidine-3-thiol;
N-(naphthalen-1-ylmethyl)-N-([2R,3R]-3-sulfanylpyrrolidin-2-ylmethyl)pentanamide;
N-(naphthalen-1-ylmethyl)-N-([2R,3R]-3-sulfanylpyrrolidin-2-ylmethyl)-2-(pyridin-3-yl)-acetamide;
N-((2R,3R)-3-sulfanyl-pyrrolidin-2-ylmethyl)-3-methyl-N-(2-(naphthalen-1-yl-ethyl)butyramide;
N-([2R,3R]-3-sulfanyl-pyrrolidin-2-ylmethyl)-N-2-(naphthalen-1-yl-ethyl)-2-pyridin-3-yl-acetamide;
(2R3R)-2-{[[(3-Methoxypropyl)-(2-naphthalen-1-ylethyl)amino]methyl}-pyrrolidine-3-thiol;
N-([2R,3R]-3-sulfanyl-pyrrolidin-2-ylmethyl)-2-(4-methoxyphenyl)-N-(2-naphthalen-2-yl-ethyl)acetamide;
(2R,3R)-2-{[[(2-(4-Methoxyphenyl)ethyl)-(2-naphthalen-1-ylethyl)amino]methyl}-pyrrolidine-3-thiol;
N-(2,2-Diphenyl-ethyl)-N-([2R,3R]-3-sulfanyl-pyrrolidin-2-ylmethyl)-3-methyl- butyramide;
N-([2R,3R]-3-sulfanyl-pyrrolidin-2-ylmethyl)-3,3-dimethyl-N-(2-naphthalen-2-yl-ethyl)-butyramide;
N-2,2-Diphenyl-ethyl)-N-([2R,3R]-3-sulfanyl-pyrrolidin-2-ylmethyl)-3,3-dimethyl-butyramide;
(2S)-2-{3-[([2R,3R]-3-sulfanyl-pyrrolidin-2-ylmethyl)-(3-methoxy-propyl)amino]-benzoylamino}-4-methylsulfanyl-butyric acid;
N-([2R,3R]-3-sulfanyl-pyrrolidin-2-ylmethyl)-3,3-dimethyl-N-(2-naphthalen-1-yl-ethyl)-butyramide;
(2S)-4-carbamoyl-2-({2-phenyl-5-[([2R,3R]-3-sulfanyl-pyrrolidin-2-ylmethyl)-amino]-phenyl carbonyl}-amino)-butyric acid;
(2S)-4-carbamoyl-2-({2-phenyl-5-[([2R,3R]-3-sulfanyl-pyrrolidin-2-ylmethyl)-amino]-phenyl carbonyl}-amino)-butyric acid methyl ester;
2-(3-pyridyl)-N-(2,2-diphenyl-ethyl)-N-((2R,3R)-3-sulfanylpyrrolidin-2-ylmethyl)-acetamide;
6methoxy-1-oxido-N-(2,2-diphenyl-ethyl)-N-((2R,3R)-3-sulfanylpyrrolidin-2-ylmethyl)-pyridine-3- carboxamide;
N-naphthyl-1-yl-ethyl)-N-([2R3R]-3-sulfanylpyrrolidin-2yl-methyl)thiazole-5- carboxamide;
6-methoxy-1-oxido-N-(naphthyl-1-yl-ethyl)-N-((2R,3R)-3-sulfanylpyrrolidin-2-ylmethyl)-pyridine-3-carboxamide;
(2S)-2-{2-benzyl-4-[([2R3R]3-sulfanyl-pyrrolidin-2-ylmethyl)-amino]-benzoylamino}-4-methylsulfanyl-butyric acid; and
(2S)-2-(2-methoxy-ethyl)-1-([2R,3R]-3-sulfanyl-pyrrolidin-2-ylmethyl)-4-naphthoyl- piperazine.

In another aspect of the present invention there is provided a compound which inhibits farnesyl-protein transferase of the formula B:

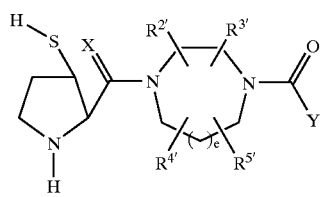

B wherein:
X is O or H$_2$;
e is 0 or 1;
t is 1 to 4;
R$^{2'}$, R$^{3'}$, R$^{4'}$, and R$^{5'}$ are independently selected from: H;
C$_{1-8}$-alkyl, alkenyl, alkynyl, aryl, heterocycle, —CO—NR$^{6'}$R$^{7'}$ or —CO—OR$^{6'}$, unsubstituted or substituted with one or more of:

1) aryl or heterocycle, unsubstituted or substituted with:
   a. $C_{1-4}$alkyl,
   b. $(CH_2)_rOR^{6'}$,
   c. $(CH_2)_rNR^{6'}R^{7'}$,
   d. halogen,
2) $C_{3-6}$cycloalkyl,
3) $OR^{6'}$,
4) $SR^{6'}$, $S(O)R^{6'}$, $SO_2R^{6'}$,
5) —$NR^{6'}R^{7'}$,
6) —$NR^{6'}$—CO—$R^{7'}$,
7) —$NR^{6'}$—CO—$NR_7R^{8'}$,
8) —O—CO—$NR^{6'}R^{7'}$,
9) —O—CO—$OR^{6'}$,
10) —O—$NR^{6'}R^{7'}$,
11) —$SO_2NR^{6'}R^{7'}$,
12) —$NR^{6'}$—$SO_2$—$R^{7'}$,
13) —CO—$R^{6'}$, or
14) —CO—$OR^{6'}$;
and any two of $R^{2'}$, $R^{3'}$, $R^{4'}$, and $R^{5'}$ are optionally attached to the same carbon atom;
Y is aryl, heterocycle, unsubstituted or substituted with one or more of:
1) $C_{1-4}$alkyl, unsubstituted or substituted with:
   a. $C_{1-4}$alkoxy,
   b. $NR^{6'}R^{7'}$,
   c. $C_{3-6}$cycloalkyl,
   d. aryl or heterocycle,
   e. HO,
2) aryl or heterocycle,
3) halogen,
4) $OR^6$,
5) $NR^{6'}R^{7'}$,
6) CN
7) $NO_2$, or
8) $CF_3$;
$R^{6'}$, $R^{7'}$ and $R^{8'}$ are independently selected from: H; $C_{1-4}$alkyl, $C_{3-6}$cycloalkyl, heterocycle, aryl, aroyl, heteroaroyl, arylsulfonyl, heteroarylsulfonyl, unsubstituted or substituted with:
a) $C_{1-4}$alkoxy,
b) aryl or heterocycle,
c) halogen,
d) HO,
e) —CO—$R^{9'}$,
f) —$SO_2R^{9'}$, or
g) $NRR^1$, wherein
$R^{6'}$ and $R^{7'}$ may be joined in a ring, and
$R^{7'}$ and $R^{8'}$ may be joined in a ring;
$R^{9'}$ is $C_{1-4}$alkyl or aralkyl;
or a optical isomer, disulfide or pharmaceutically acceptable salt thereof.

A preferred subclass of the formula B is:

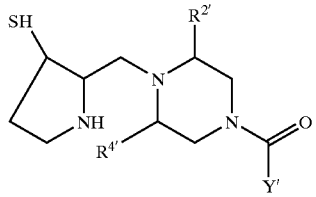

wherein $R^{2'}$ and $R^{4'}$ are independently hydrogen and Y' is $C_{1-4}$alkyl, phenyl or a 5 or 6 membered heteroaryl ring containing up to 3 heteroatoms selected from N, O and S or of the formula —$C_{1-4}$alkyl $OR^{10'}$ wherein $R^{10'}$ is $C_{1-4}$alkyl, phenyl or 5 or 6-membered heteroaryl containing up to 3 heteroatoms selected from N, O and S. Preferably $R^{10'}$ is $C_{1-4}$alkyl.

Preferably Y' is naphthyl.

The aspect of the invention relating to Formula B involves compounds related to those disclosed PCT patent application WO 95/00497 (Graham et al.); see the complete specification and claim 1 in particular. Formula B above is based on Formula A in WO 95/00497 (Graham et al.) but with the 3-sulfanylpyrrolidine moiety of the present invention replacing the cysteine-like moiety on the left hand side of Formula A in WO 95100497 (Graham et al.). Optionally the nitrogen and/or thiol atoms in the pyrrolidine moiety of Formula B may be substituted by taking the values for $R^1$ and $R^2$ in Formula I as set out herein. Compounds within the scope of Formula B may be prepared by a skilled person using the synthetic details in WO 95/00497 (Graham et al.) combined with the present specification. Preferred compounds for this aspect of the invention correspond to those set out in claims 6–12 of WO 95/00497 (Graham et al.) but with the 3-sulfanylpyrrolidin-2-yl-methyl moiety of the present invention replacing the $HS$—$CH_2$—$CH(NH_2)$—CH— moiety on the left hand side of the relevant compounds attached to the piperazine ring as drawn out in the claims. A preferred compound is (2S)-2-(2-methoxy-ethyl)-1-([2R,3R]-3-sulfanyl-pyrrolidin-2-ylmethyl)-4-naphthoyl-piperazine; see Example 7 herein.

Compounds of Formula I and III–V may form salts which are within the ambit of the invention. Pharmaceutically acceptable salts are preferred although other salts may be useful in, for example, isolating or purifying compounds.

When the compound contains a basic moiety it may form pharmaceutically acceptable salts with a variety of inorganic or organic acids, for example hydrochloric, hydrobromic, sulphuric, phosphoric, trifluoroacetic, citric or maleic acid. A suitable pharmaceutically-acceptable salt of the invention when the compound contains an acidic moiety is an alkali metal salt, for example a sodium or potassium salt, an alkaline earth metal salt, for example a calcium or magnesium salt, an ammonium salt or a salt with an organic base which affords a pharmaceutically-acceptable cation, for example a salt with methylamine, dimethylamine, trimethylamine, piperidine, morpholine or tris-(2-hydroxyethyl)amine.

Solvates, for example hydrates, are also within the ambit of the invention and may be prepared by generally known methods.

Various forms of prodrugs are well known in the art. For examples of such prodrug derivatives, see:

a) Design of Prodrugs, edited by H. Bundgaard, (Elsevier, 1985) and Methods in Enzymology. Vol. 42, p. 309–396, edited by K Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

Examples of pro-drugs include in vivo hydrolysable esters of a compound of the Formula I. An in vivo hydrolysable ester of a compound of the formula (I) containing carboxy group is, for example, a pharmaceutically-acceptable ester which is hydrolysed in the human or animal body to produce the parent acid. Suitable pharmaceutically-acceptable esters for carboxy include $C_{1-6}$alkoxymethyl esters for example methoxymethyl, $C_{1-6}$alkanoyloxymethyl esters for example pivaloyloxymethyl, phthalidyl esters, $C_{3-8}$cycloalkoxycarbonyloxy$C_{1-6}$alkyl esters for example 1-cyclohexylcarbonyloxyethyl; 1,3-dioxolen-2-onylmethyl esters for example 5-methyl-1,3-dioxolen-2-onylmethyl; and $C_{1-6}$alkoxycarbonyloxyethyl esters for example 1-methoxycarbonyloxyethyl and may be formed at any carboxy group in the compounds of this invention.

According to another aspect of the invention there is provided a pharmaceutical composition comprising a compound as defined in Formula I or an individual compound listed above together with a pharmaceutically acceptable diluent or carrier. A preferred pharmaceutical composition is in the form of a tablet.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

Suitable pharmaceutically acceptable excipients for a tablet formulation include, for example, inert diluents such as lactose, sodium carbonate, calcium phosphate or calcium carbonate, granulating and disintegrating agents such as corn starch or algenic acid; binding agents such as starch; lubricating agents such as magnesium stearate, stearic acid or talc; preservative agents such as ethyl or propyl p-hydroxybenzoate, and anti-oxidants, such as ascorbic acid. Tablet formulations may be uncoated or coated either to modify their disintegration and the subsequent absorption of the active ingredient within the gastrointestinal tract, or to improve their stability and/or appearance, in either case, using conventional coating agents and procedures well known in the art.

Compositions for oral use may be in the form of hard gelatin capsules in which the active ingredient is mixed with an inert solid diluent, for example, calcium carbonate, calcium phosphate or kaolin, or as soft gelatin capsules in which the active ingredient is mixed with water or an oil such as peanut oil, liquid paraffin, or olive oil.

Aqueous suspensions generally contain the active ingredient in finely powdered form together with one or more suspending agents, such as sodium carboxymethylcellulose, methylcellulose, hydroxypropylmethylcellulose, sodium alginate, polyvinyl-pyrrolidone, gum tragacanth and gum acacia; dispersing or wetting agents such as lecithin or condensation products of an alkylene oxide with fatty acids (for example polyoxethylene stearate), or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives (such as ethyl or propyl p-hydroxybenzoate, anti-oxidants (such as ascorbic acid), colouring agents, flavouring agents, and/or sweetening agents (such as sucrose, saccharine or aspartame).

Oily suspensions may be formulated by suspending the active ingredient in a vegetable oil (such as arachis oil, olive oil, sesame oil or coconut oil) or in a mineral oil (such as liquid paraffin). The oily suspensions may also contain a thickening agent such as beeswax, hard paraffin or cetyl alcohol. Sweetening agents such as those set out above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water generally contain the active ingredient together with a dispersing or wetting agent, suspending agent and one or more preservatives. Suitable dispersing or wetting agents and suspending agents are exemplified by those already mentioned above. Additional excipients such as sweetening, flavouring and colouring agents, may also be present.

The pharmaceutical compositions of the invention may also be in the form of oil-in-water emulsions. The oily phase may be a vegetable oil, such as olive oil or arachis oil, or a mineral oil, such as for example liquid paraffin or a mixture of any of these. Suitable emulsifying agents may be, for example, naturally-occurring gums such as gum acacia or gum tragacanth, naturallyoccurring phosphatides such as soya bean, lecithin, an esters or partial esters derived from fatty acids and hexitol anhydrides (for example sorbitan monooleate) and condensation products of the said partial esters with ethylene oxide such as polyoxyethylene sorbitan monooleate. The emulsions may also contain sweetening, flavouring and preservative agents.

Syrups and elixirs may be formulated with sweetening agents such as glycerol, propylene glycol, sorbitol, aspartame or sucrose, and may also contain a demulcent, preservative, flavouring and/or colouring agent.

The pharmaceutical compositions may also be in the form of a sterile injectable aqueous or oily suspension, which may be formulated according to known procedures using one or more of the appropriate dispersing or wetting agents and suspending agents, which have been mentioned above. A sterile injectable preparation may also be a sterile injectable solution or suspension in a non-toxic parenterally-acceptable diluent or solvent, for example a solution in 1,3-butanediol.

Suppository formulations may be prepared by mixing the active ingredient with a suitable non-irritating excipient which is solid at ordinary temperatures but liquid at the rectal temperature and will therefore melt in the rectum to release the drug. Suitable excipients include, for example, cocoa butter and polyethylene glycols.

Topical formulations, such as creams, ointments, gels and aqueous or oily solutions or suspensions, may generally be obtained by formulating an active ingredient with a conventional, topically acceptable, vehicle or diluent using conventional procedure well known in the art.

Compositions for administration by insufflation may be in the form of a finely divided powder containing particles of average diameter of, for example, 30μ or much less, the powder itself comprising either active ingredient alone or diluted with one or more physiologically acceptable carriers such as lactose. The powder for insufflation is then conveniently retained in a capsule containing, for example, 1 to 50 mg of active ingredient for use with a turbo-inhaler device, such as is used for insufflation of the known agent sodium cromoglycate.

Compositions for administration by inhalation may be in the form of a conventional pressurised aerosol arranged to dispense the active ingredient either as an aerosol containing finely divided solid or liquid droplets. Conventional aerosol propellants such as volatile fluorinated hydrocarbons or hydrocarbons may be used and the aerosol device is conveniently arranged to dispense a metered quantity of active ingredient.

For further information on Formulation the reader is referred to Chapter 25.2 in Volume 5 of Comprehensive Medicinal Chemistry (Corwin Hansch; Chairman of Editorial Board), Pergamon Press 1990.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 2 g of active agent compounded with an appropriate and convenient amount of excipients which may vary from about 5 to about 98 percent by weight of the total composition. Dosage unit forms will generally contain about 1 mg to about 500 mg of an active ingredient. For further information on Routes of Administration and Dosage Regimes the reader is referred to Chapter 25.3 in Volume 5 of Comprehensive Medicinal Chemistry (Corwin Hansch; Chairman of Editorial Board), Pergamon Press 1990.

The size of the dose for therapeutic or prophylactic purposes of a compound of the Formula I will naturally vary according to the nature and severity of the conditions, the age and sex of the animal or patient and the route of administration, according to well known principles of medicine. As mentioned above, compounds of the Formula I are useful in treating diseases or medical conditions which are due alone or in part to the effects of farnesylation of ras.

In using a compound of the Formula I for therapeutic or prophylactic purposes it will generally be administered so that a daily dose in the range, for example, 0.5 mg to 75 mg per kg body weight is received, given if required in divided doses. In general lower doses will be administered when a parenteral route is employed. Thus, for example, for intravenous administration, a dose in the range, for example, 0.5 mg to 30 mg per kg body weight will generally be used. Similarly, for administration by inhalation, a dose in the range, for example, 0.5 mg to 25 mg per kg body weight will be used. Oral administration is however preferred.

Compounds of this invention may be useful in combination with known anti-cancer and cytotoxic agents. If formulated as a fixed dose such combination products employ the compounds of this invention within the dosage range described herein and the other pharmaceutically active agent within its approved dosage range. Sequential use is contemplated when a combination formulation is inappropriate.

According to another aspect of the invention there is provided a compound of Formula I, or a pharmaceutically-acceptable salt thereof, for use as a medicament.

According to another aspect of the invention there is provided a compound of Formula I, or a pharmaceutically-acceptable salt thereof, for use in preparation of a medicament for treatment of a disease mediated through farnesylation of ras.

According to another aspect of the present invention there is provided a method of treating ras mediated diseases, especially cancer, by administering an effective amount of a compound of Formula I, or a pharmaceutically-acceptable salt thereof, to a mammal in need of such treatment.

Diseases or medical conditions may be mediated alone or in part by farnesylated ras. A particular disease of interest is cancer. Specific cancers of interest include:
carcinoma, including that of the bladder, breast, colon, kidney, liver, lung, ovary, pancreas, stomach, cervix, thyroid and skin;
hematopoietic tumors of lymphoid lineage, including acute lymphocytic leukemia, B-cell lymphoma and Burketts lymphoma;
hematopoietic tumors of myeloid lineage, including acute and chronic myelogenous leukemias and promyelocytic leukemia;
tumors of mesenchymal origin, including fibrosarcoma and rhabdomyosarcoma; and
other tumors, including melanoma, seminoma, teratocarcinoma, neuroblastoma and glioma.

The compounds of Formula I are especially useful in treatment of tumors having a high incidence of ras mutation, such as colon, lung, and pancreatic tumors. By the administration of a composition having one (or a combination) of the compounds of this invention, development of tumors in a mammalian host is reduced.

Compounds of Formula I may also be useful in the treatment of diseases other than cancer that may be associated with signal transduction pathways operating through Ras, e.g., neuro-fibromatosis.

Compounds of Formula I may also be useful in the treatment of diseases associated with CAAX-containing proteins other than Ras (e.g., nuclear lamins and transducin) that are also post-translationally modified by the enzyme farnesyl protein transferase.

Although the compounds of the Formula I are primarily of value as therapeutic agents for use in warm-blooded animals (including man), they are also useful whenever it is required to inhibit the effects of activation of ras by farnesylation. Thus, they are useful as pharmacological standards for use in the development of new biological tests and in the search for new pharmacological agents.

According to another aspect of the invention there is provided a process for preparing compounds Formula I as defined above which comprises deprotecting a compound of Formula VI:

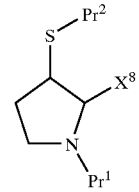

Formula VI wherein $X^8$ represents the right hand side of the Formula I, $Pr^1$ is H or an amino protecting group, $Pr^2$ is H or a thio protecting group and any functional groups in $X^8$ are optionally protected with the proviso that there is at least one protecting group and optionally, if desired. converting the product thus obtained into a pharmaceutically acceptable salt thereof.

Compounds outside the scope of Formula I having a 4-sulfanyl pyrrolidine moiety (compared with the 3-sulfanyl pyrrolidine moiety of the present invention) are known as intermediates in carbapenem side chain synthesis. The reader is referred to the following publications in this regard in respect of background synthetic details for assistance in compound preparation: Matsumura, Heterocycles (1995), 41, 147–59; European patent application EP 590885 (Zeneca; Betts et al); European patent application EP 592167 (Zeneca; Siret); European patent application EP 562855 (Zeneca; Jung el al); International patent application WO 92/17480 (Imperial Chemical Industries; Betts et al); European patent application EP 508682 (Imperial Chemical Industries; Betts et al); European Patent Application EP 280771 (Fujisawa Pharmaceutical, Murata et al); and International patent application WO 92/17479 (Imperial Chemical Industries; Betts el al).

A compound of the invention, or a salt thereof, may be prepared by any process known to be applicable to the preparation of such compounds or structurally related compounds. Such processes are illustrated by the following representative schemes in which variable groups have any of the meanings defined for Formula I unless stated otherwise. Functional groups may be protected and deprotected using conventional methods. For examples of protecting groups such as amino and carboxylic acid protecting groups (as well as means of formation and eventual deprotection), see T. W. Greene and P. G. M. Wuts, "Protective Groups in Organic Synthesis", Second Edition, John Wiley & Sons, New York, 1991. Note abbreviations used have been listed immediately before the Examples below.

Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower" signifies that the group to which it is applied preferably has 1–4 carbon atoms. It will be understood that these examples are not exhaustive. Where specific examples of methods for the removal of protecting groups arc given below these are similarly not exhaustive. The use of protecting groups and methods of deprotection not specifically mentioned is of course within the scope of the invention.

A carboxy protecting group may be the residue of an ester-forming aliphatic or araliphatic alcohol or of an ester-forming silanol (the said alcohol or silanol preferably containing 1–20 carbon atoms).

Examples of carboxy protecting groups include straight or branched chain (1–12C)alkyl groups (e.g. isopropyl, t-butyl); lower alkoxy lower alkyl groups (e.g. methoxymethyl, ethoxymethyl, isobutoxymethyl; lower aliphatic acyloxy lower alkyl groups, (e.g. acetoxymethyl, propionyloxymethyl, butyryloxymethyl, pivaloyloxymethyl); lower alkoxycarbonyloxy lower alkyl groups (e.g. 1-methoxycarbonyloxyethyl, 1-ethoxycarbonyloxyethyl); aryl lower alkyl groups (e.g. p-methoxybenzyl, o-nitrobenzyl, p-nitrobenzyl, benzhydryl and phthalidyl); tri(lower alkyl)silyl groups (e.g. trimethylsilyl and t-butyldimethylsilyl); tri(lower alkyl)silyl lower alkyl groups (e.g. trimethylsilylethyl); and (2–6C)alkenyl groups (e.g. allyl and vinylethyl).

Methods particularly appropriate for the removal of carboxyl protecting groups include for example acid-, metal- or enzymically-catalysed hydrolysis.

Examples of hydroxy protecting groups include lower alkenyl groups (e.g. allyl); lower alkanoyl groups (e.g. acetyl); lower alkoxycarbonyl groups (e.g. 1-butoxycarbonyl); lower alkenyloxycarbonyl groups (e.g. allyloxycarbonyl); aryl lower alkoxycarbonyl groups (e.g. benzoyloxycarbonyl, p-methoxybenzyloxycarbonyl, o-nitrobenzyloxycarbonyl, p-nitrobenzyloxycarbonyl); tri lower alkyl/arylsilyl groups (e.g. trimethylsilyl, t-butyldimethylsilyl, t-butyldiphenylsilyl); aryl lower alkyl groups (e.g. benzyl) groups; and triaryl lower alkyl groups (e.g. triphenylmethyl).

Examples of amino protecting groups include formyl, aralkyl groups (e.g. benzyl and substituted benzyl, e.g. p-methoxybenzyl, nitrobenzyl and 2,4-dimethoxybenzyl, and triphenylmethyl); di-p-anisylmethyl and furylmethyl groups; lower alkoxycarbonyl (e.g. t-butoxycarbonyl); lower alkenyloxycarbonyl (e.g. allyloxycarbonyl); aryl lower alkoxycarbonyl groups (e.g. benzyloxycarbonyl, p-methoxybenzyloxycarbonyl, o-nitrobenzyloxycarbonyl, p-nitrobenzyloxycarbonyl; trialkylsilyl (e.g. trimethylsilyl and t-butyldimethylsilyl); alkylidene (e.g. methylidene); benzylidene and substituted benzylidene groups.

Methods appropriate for removal of hydroxy and amino protecting groups include, for example, acid-, base, metal- or enzymically-catalysed hydrolysis, or photolytically for groups such as o-nitrobenzyloxycarbonyl, or with fluoride ions for silyl groups.

Examples of thiol protecting groups include aryl lower alkyl (e.g. benzyl, p-methoxybenzyl and p-nitrobenzyl); diphenylmethyl; triphenylmethyl; lower alkanoyl (e.g. acetyl); benzoyl lower alkoxycarbonyl (e.g. tert-butoxycarbonyl); benzyloxycarbonyl; and tert-butyl.

Examples of protecting groups for amide groups include aralkoxymethyl (e.g. benzyloxymethyl and substituted benzyloxymethyl); alkoxymethyl (e.g. methoxymethyl and trimethylsilylethoxymethyl); tri alkyl/arylsilyl (e.g. trimethylsilyl, t-butyldimethylsily, t-butyldiphenylsilyl); tri alkyl/arylsilyloxymethyl (e.g. t-butyldimethylsilyloxymethyl, t-butyldiphenylsilyloxymethyl); 4-alkoxyphenyl (e.g. 4-methoxyphenyl); 2,4-di(alkoxy)phenyl (e.g. 2,4-dimethoxyphenyl); 4-alkoxybenzyl (e.g. 4-methoxybenzyl); 2,4-di(alkoxy)benzyl (e.g. 2,4-di(methoxy)benzyl); and alk-1-enyl (e.g. allyl, but-1-enyl and substituted vinyl e.g. 2-phenylvinyl).

Aralkoxymethyl, groups may be introduced onto the amide group by reacting the latter group with the appropriate aralkoxymethyl chloride, and removed by catalytic hydrogenation. Alkoxymethyl, tri alkyl/arylsilyl and tri alkyl/silyloxymethyl groups may be introduced by reacting the amide with the appropriate chloride and removing with acid; or in the case of the silyl containing groups, fluoride ions. The alkoxyphenyl and alkoxybenzyl groups are conveniently introduced by arylation or alkylation with an appropriate halide and removed by oxidation with ceric ammonium nitrate. Finally alk-1-enyl groups may be introduced by reacting the amide with the appropriate aldehyde and removed with acid.

Compounds of Formula I in which G represents —CO—NR$^{16}$— may be prepared by forming an amide bond between compounds 1 and 2 as outlined in Scheme 1. Compounds of Formula I in which G represents —CO—NR$^{16}$-T- may be prepared by an analogous procedure. Suitable coupling conditions include the following.

i) Use of EEDQ at ambient temperature in an organic solvent (e.g. dichloromethane, methanol).

ii) Use of oxalyl chloride in an organic solvent (e.g. $CH_2Cl_2$), DMF in a catalytic amount, in the presence of an organic base (e.g. NMM, triethylamine, DMAP) at 0° C. to ambient temperature for 0.5–16 h.

iii) Use of EDC/HOBT in an organic solvent (e.g. DMF, $CH_2Cl_2$).

iv) Use of DCCI/HOBT in an organic solvent (e.g. DMF, $CH_2Cl_2$) in the presence of an organic base (e.g. triethylamine).

v) Use of mixed anhydride reactions under standard conditions, for example isopropylchloroformate in an organic solvent (e.g. DMF, DMA, dichloromethane) in the presence of an organic base (e.g. NMM, DMAP, triethylamine).

vi) Via an active ester under standard conditions e.g. pentafluorophenyl ester in an organic solvent (e.g. dichloromethane) in the presence of an organic base (e.g. triethylamine).

vii) Via an acid chloride under standard conditions e.g. using thionyl chloride and heat for about 150 min followed by an organic base (e.g. triethylamine) in the presence of an organic solvent (e.g. acetonitrile).

Compounds of Formula I in which G represents —$CH_2NR^{16}$—, —$CH_2O$— or —$CH_2S$— may be prepared as outlined in Scheme 2. LG represents a leaving group (e.g. mesyloxy, tosyloxy, halogen) and X represents S, O or $NR^{16}$. Suitable coupling conditions include the following.

i) Use of an inorganic base (e.g. $NaHCO_3$, NaH, $K_2CO_3$, butyllithium) in an organic solvent (e.g. THF, DMF, DMSO) and a temperature of about 65° to 150° C.

ii) Use of an organic base (e.g. triethylamine, DMAP) in an organic solvent (e.g. THF, dichloromethane, DMA, DMF) at a temperature range of room temperature –150° C.

iii) Use of an inorganic base (e.g. KOH, NaOH, $K_2CO_3$) in an aqueous (e.g. water) and organic solvents (e.g. dichloromethane) in a 2 phase system, optionally in the presence of a phase transfer catalyst (e.g. tetrabutylammoniumbromide).

Compounds of Formula I in which G represents —CH=$CR^{16}$— may be prepared using a Wittig reaction as outlined in Scheme 3. Suitable reaction conditions include the following.

i) Use of a base (e.g. potassium carbonate, metal hydride, metal alkoxide) in the presence of an organic solvent (e.g. THF, toluene, DMSO) optionally in the presence of an aqueous solvent (2-phase system) and optionally in the presence of a catalyst complexing agent which solubilises alkali metal ions in non-polar solvents such as 1,4,7,10,13-pentaoxacyclopentadecane (also called 15-Crown-5) or 1,4,7,10,13,16-hexaoxacyclooctadecane (also called 18-Crown-6).

Compounds of Formula I in which G represents —$CH_2$—$NR^{16}$— may be prepared as outlined in Scheme 4 by coupling aldehyde (2) with compound 4. Suitable coupling conditions include the following.

i) Use of a reducing agent (e.g. $NaCNBH_3$, $BH_3$, hydrogen plus catalyst, $LiHBEt_3$, di-isobutyl-aluminiumhydride, lithium aluminium hydride, sodium borohydride) in the presence of a suitable solvent e.g. ethanol and acetic acid.

Aldehyde (2) may be prepared by oxidation of the corresponding alcohol (1) under suitable conditions such as use of an oxidising agent (e.g. TPAP, NMM-O) in the presence of an organic solvent (e.g. acetonitrile, dichloromethane) at room temperature. Other suitable oxidising agents include chromium oxide, pyridinium chlorochromate, pyridinium dichromate, sodium dichromate, pyridine sulfur trioxide complex and sodium hypochlorite.

Aldehyde (2) may also be prepared by reduction of the corresponding ester (1) under standard conditions using for example diisobutyl-aluminium hydride. Alternatively, aldehyde (2) may be prepared by reducing the appropriate N-methoxy-N-methylcarboxamide with a strong reducing agent such as lithium aluminum hydride.

Compounds of Formula I in which G represents —$CH_2$—$NR^{16}$-T-, —$CH_2$—O-T- or —$CH_2$—S-T- may be prepared as outlined in Scheme 5 in which LG represents a leaving group (e.g. mesyloxy, tosyloxy, halogen) and X represents O, S or $NR^{16}$. Suitable coupling conditions are as outlined above in relation to Scheme 2. Optionally the positions of LG and XH in compounds 1 and 2 in Scheme 5 can be reversed to give the same end product.

Compounds of Formula I in which G represents —$CH_2$—$NR^{16}$—$SO_2$— may be prepared as outlined in Scheme 6. Compounds 1 and 2 may be coupled under standard conditions such as the following.

i) Use of an organic base (e.g. di-isopropyl-ethylamine, triethylamine, 4-methyl-morpholine) in the presence of an organic solvent (e.g. dichloromethane) at a temperature range of 0°–40° C.

ii) Use of an inorganic base (e.g. potassium carbonate) in the presence of an organic solvent (e.g. DMF) at a temperature range of 0°–150° C.

Compounds of Formula I in which G represents —$CH_2$—$NR^{16}$—CO-T- may be prepared as outlined in Scheme 7. Compounds 1 and 2 may be coupled under standard conditions such as described above for G=—CO—$NR^{16}$—.

Compounds of Formula I in which G represents —$CH_2$—$CHR^{16}$— may be prepared by reduction of compounds of the type set out as compound 3 in Scheme 3. Reduction is carried out under standard conditions with standard reagents for example using hydrogenation in the presence of a catalyst such as palladium on charcoal at ambient temperature.

Compounds of the formula I in which G represents —$CH_2NR^{16}$—, —$CONR^{16}$, $CH_2N(R^{16})$-T- or —$CH_2N(R^{16})COT$- wherein $R^{16}$ is not hydrogen, may be prepared from the appropriate compound of the formula I wherein $R^{16}$ is hydrogen by introducing the appropriate $R^{16}$ by acylation, alkylation etc. For example, by using similar methods to those disclosed in the specific examples.

Scheme 1

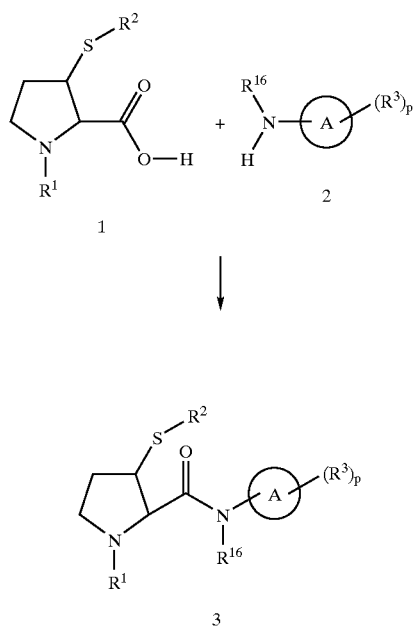

Scheme 2
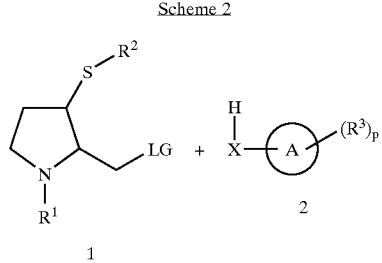
Scheme 3
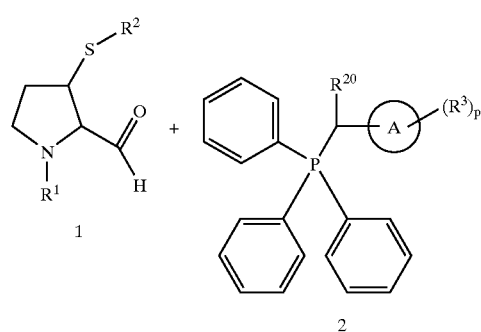
Scheme 4
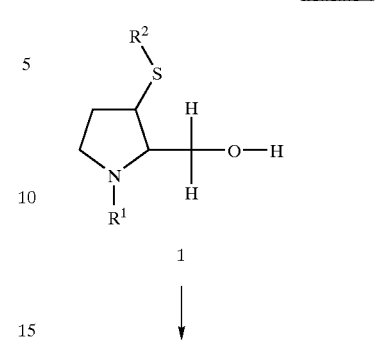
Scheme 5
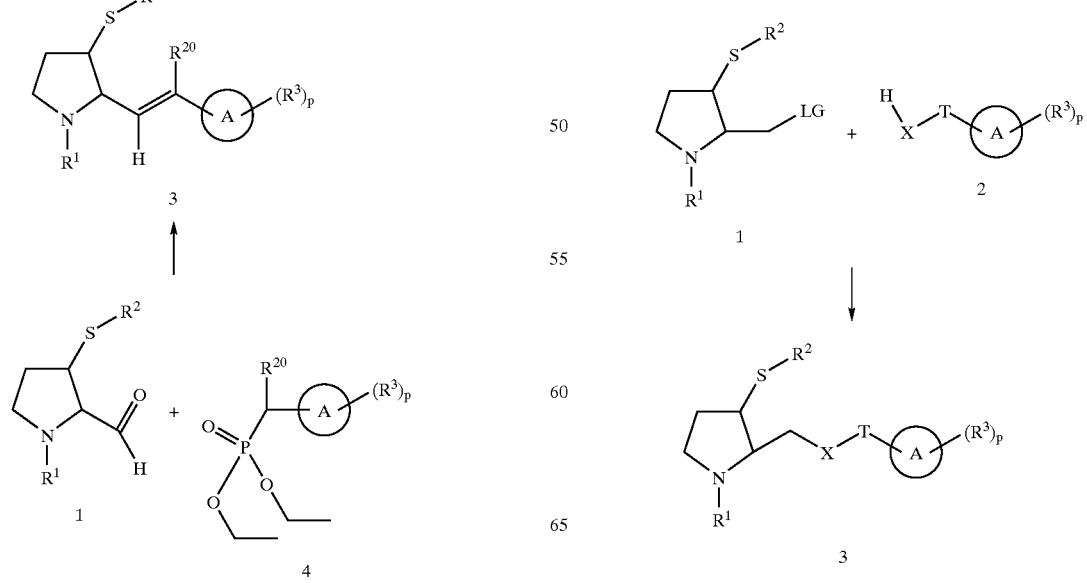

Scheme 6

[Scheme 6 chemical structures showing compound 1 (pyrrolidine with S-R², N-H, N-R²³, N-R¹ substituents) plus compound 2 (Cl-SO₂-A-(R³)ₚ) reacting to form compound 3 (sulfonamide product).]

Scheme 7

[Scheme 7 chemical structures showing compound 1 (pyrrolidine with S-R², N-H, N-R²⁴, N-R¹ substituents) plus compound 2 (HO-T-A-(R³)ₚ carboxylic acid) reacting to form compound 3 (amide product).]

Biological activity was tested as follows. Farnesyl protein transferase (FPT) was partially purified from human placenta by ammonium sulphate fractionation followed by a single Q-Sepharose® (Pharmacia, Inc) anion exchange chromatography essentially as described by Ray and Lopez-Belmonte (Ray K P and Lopez-Belmonte J (1992) Biochemical Society Transations 20 494–497). The substrate for FPT was Kras (CVIM C-terminal sequence). The cDNA for oncogenic val12 variant of human c-Ki-ras-2 4B was obtained from the plasmid pSW11-1 (ATCC). This was then subcloned into the polylinker of a suitable expression vector e.g. pIC147. The Kras was obtained after expression in the *E. coli* strain, BL21. The expression and purification of c-KI-ras-2 4B and the val12 variant in *E. coli* has also been reported by Lowe et al (Lowe P N et al. J. Biol. Chem. (1991) 266 1672–1678).

Incubations with enzyme contained 300 nM tritiated farnesyl pyrophosphate (DuPont/New England Nuclear), 120 nM ras-CVIM, 50 mM Tris HCl pH 8.0, 5 mM MgCl$_2$, 10 $\mu$M ZnCl$_2$, 5 mM dithiotheitol and compounds were added at appropriate concentrations in DMSO (3% final concentration in test and vehicle control). Incubations were for 20 minutes at 37° and were stopped with acid ethanol as described by Pompliano et al. (Pompliano D L et al (1992) 31 3800–3807). Precipitated protein was then collected onto glass fibre filter mats (B) using a Tomte® cell harvester and tritiated label was measured in a Wallac®1204 Betaplate scintillation counter.

Although the pharmacological properties of the compounds of the Formula I vary with structural change as expected, in general compounds of the Formula I possess an IC$_{50}$ in the above test in the range, for example, 0.001 to 200 $\mu$M. Thus by way of example the compound of Example 2 herein has an IC$_{50}$ of approximately 0.42 $\mu$M.

No physiologically unacceptable toxicity was observed at the effective dose for compounds tested of the present invention.

The invention will now be illustrated in the following non-limiting Examples in which, unless otherwise stated:

(i) evaporations were carried out by rotary evaporation in vacuo and work-up procedures were carried out after removal of residual solids by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) the end-products of the Formula I have satisfactory microanalyses and their structures were confirmed by nuclear magnetic resonance (NMR) and mass spectral techniques; chemical shift values were measured on the delta scale; the following abbreviations have been used: s, singlet; d, doublet; t or tr, triplet; m, multiplet; br, broad;

(vi) intermediates were not generally fully characterised and purity was assessed by thin layer chromatographic, infra-red (IR) or NMR analysis;

(vii) the following abbreviations have been used:
BOC tert-butoxycarbonyl
DCCI 1,3-dicyclohexylcarbodiimide
DMA N,N-dimethylacetamide
DMAP 4-dimethyl-aminopyridine
DMF N,N-dimethylformamide
DMSO dimethylsulfoxide
EDC 1-(3-dimethylaminopropyl)-3-ethyl-carbodiimide
EEDQ 2-ethoxy-1-ethoxycarbonyl-1,2-dihydroquinoline
HOBT 1-hydroxybenzotriazole
NMM N-methylmorpholine
NMM-O 4-methylmorpholine-N-oxide
TFA trifluoroacetic acid
THF tetrahydrofuran
TMSI trimethylsilyliodide
TPAP tetrapropylammonium perruthenate Note in the Schemes only those hydrogen atoms thought to assist clarity have been illustrated (ie not all hydrogen atoms have been illustrated).

EXAMPLE 1

3-methyl-N-(2,2-diphenyl-ethyl)-N-(cis)-3-sulfanylpyrrolidin-2-ylmethyl)butyramide (compound 14a)

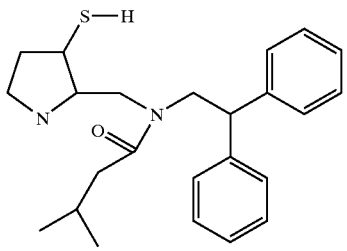

1. A solution of starting material 3-methyl-N-(2,2-diphenyl-ethyl)-N-((cis)-1-BOC-3-tritylsulfanyl-pyrrolidin-2-ylmethyl)butyramide (compound 12a; 0.265 g), triethylsilane (0.25 ml) in dichloromethane (2 ml) was treated with trifluoroacetic acid (16 ml) and the mixture stirred under an argon atmosphere for 30 minutes at ambient temperature and then evaporated under reduced pressure to remove most of the solvents. The residue was taken up in ethyl acetate (2 ml) and treated with 1.0M ethereal HCl. The ethyl acetate was evaporated away and diethyl ether (5 ml) and iso-hexane (20 ml) were added. The gummy solid obtained gradually solidified and was isolated on a centrifuge, washed with more ether (5 ml)/iso-hexane (20 ml) and dried under high-vacuum to give the title compound as a white solid (0.125 g).

NMR (CDCl$_3$) δ: 0.80–0.95(m,6H), 1.85–2.50(m,6H), 3.00–3.15(m,1H), 3.30–3.60(m,3H), 3.75–4.30(m,4H), 7.20–7.40(m,10H), 7.60(br.s,1H), 8.67(br.s,1H), 11.20(br.s, 1H) Micro Analysis % Theory C, 65.2; H, 7.89; N, 6.19. (1.0 HCl, 0.5 H$_2$O,0.14Ethyl ether) % Found C, 65.2; H, 8.00; N, 6.0.

The starting material was prepared as follows.

2. 3-Tritylsulfanyl-pyrrolidine-2-carboxylic acid (compound 4) was prepared from methyl 3-bromo-1-pyrrolin-2-carboxylate (compound 1) by the route described in Liebigs Ann. Chem. 1981, 1073–1088. In brief, the methyl ester of the 2-carboxylate group of compound 1 was converted to the sodium salt of the carboxylic acid using aqueous sodium hydroxide solution at 0–5°; the sodium 3-bromo dihydropyrrole was then converted to sodium 3-tritylsulfanyl-1-pyrrolin-2carboxylate using triphenylmethylmercaptan in the presence of DME and aqueous sodium hydroxide solution at 0–5° C.; then compound (4) was formed by using sodium borohydride and the pH adjusted to 5–6 with 1M HCl.

Di-tert-butyl dicarbonate (0.24 g) was added to a stirred mixture of compound (4) (0.39 g) and triethylamine (0.31 ml) in dichloromethane (3 ml) cooled to 0° C. under an argon atmosphere. The mixture was allowed to warm up to ambient temperature and stirred for 60 h. It was then washed with 1.0M aqueous citric acid, brine and dried. The solvent was evaporated under reduced pressure to give 1-BOC-3-tritylsulfanyl-pyrrolidine-2-carboxylic acid (5) as a solid foam (0.446 g).

3. A mixture of 1-hydroxybenzotriazole (0.142 g), EDC (0.192 g), 4-methylmorpholine (0.24 ml) and compound 5 (0.446 g) in dichloromethane (10 ml) was stirred at 5° C. for 20 minutes and then for 16 h. at ambient temperature. The mixture was then washed with 1.0M aqueous citric acid and brine, dried and the solvent evaporated under reduced pressure. The product was purified by column chromatography eluting with ethyl acetate/iso-hexane (15:85) to give 1-(1-BOC-3-tritylsulfanyl-pyrrolidin-2-carbonyl)benzotriazole (compound 6) as a solid foam (0.193 g).

NMR (CDCl$_3$) δ:1.45+1.49(s,s,9H), 2.17–2.40(m,2H), 3.08–3.27(m,2H), 3.50–3.72(m,2H), 7.21–7.61(m,18H), 8.02(dd,1H)

4. A mixture of compound 6 (0.087 g), N,O-dimethylhydroxylamine HCl (0.028 g) and 4-dimethylaminopyridine (0.039 g) in dichloromethane (2 ml) was stirred at ambient temperature for 16 h. More N,O-dimethylhydroxylamine (0.056 g) and DMAP (0.078 g) were added and the stirring was continued for another 16 h. The reaction was filtered and the filtrate applied directly to a chromatography column which was eluted with ethyl acetate/iso-hexane (15:85) to give (cis) 1-BOC-3-tritylsulfanyl-N-methoxy-N-methylpyrrolidine-2-carboxamide (compound 8) as a white solid (0.06 g). (Note the trans stereoisomer was also formed compound 7) and isolated by column chromatography. The trans isomer was eluted from the column after the cis.

NMR (CDCl$_3$) δ:0.90–1.05(m,1H), 1.37+1.39(s,s,9H), 1.95–2.15(m,1H), 2.80–3.05(m,2H), 3.27+3.30(s,s,3H), 3.35–3.53(m,1H), 3.83+3.98(s,s,3H), 4.80–5.15(m,1H), 7.15–7.50(m,15H).

5. A solution of lithium aluminium hydride (70 ml) in diethyl ether(1.0M) was added dropwise over 10 minutes to a stirred solution of compound 8 (3.35 g) in THF (35 ml) cooled to −10° C. under an argon atmosphere. After the addition was complete the reaction was allowed to warm to +5° C. for 10 minutes and then cooled to −35° C. A solution of potassium bisulphate (1.72 g in 6 ml water) was carefully added and the mixture was then allowed to warm to ambient temperature and stirred for a further 1 h. It was then filtered through diatomaceous earth (Celite™) and the filtrate diluted with diethyl ether (50 ml). The organic solution was washed with 10% aqueous citric acid, saturated aqueous sodium bicarbonate, brine, dried and the solvent removed under reduced pressure to give (cis)-1-BOC-3-tritylsulfanyl-pyrrolidin-2-carbaldehyde (compound 9) as a solid foam (3.04 g).

NMR (CDCl$_3$) δ:1.32+1.37(s,s,9H), 1.65–2.05(m,2H), 3.00–3.70(m,4H), 7.20–7.53(m,15H), 9.42+9.54(s,s,1H)

6. Compound 9 (0.5 g) in dichloromethane (5 ml) was added to a stirred mixture of 2,2-diphenylethylamine (0.25 g), powdered 4 A molecular sieve (1.0 g) and sodium triacetoxy borohydride (0.27 g) in dichloromethane (20 ml) cooled to −20 ° C. under an argon atmosphere. The reaction mixture was then allowed to warm to ambient temperature and stirred for another 18 h. The mixture was filtered through diatomaceous earth and the filtrate washed with saturated aqueous sodium bicarbonate solution and brine. The organic solution was dried and then the solvent evaporated under reduced pressure. The residue was purified by column chromatography on silica eluting with ethyl acetate/iso-hexane (20:80), followed by (30:70) to give (cis)-1-BOC-N-(2,2-diphenylethyl)-3-tritylsulfanyl-pyrrolidin-2-yl-methylamine (compound 10) as a foam(0.547 g).

NMR (CDCl$_3$) δ:1.32+135(s,s,9H), 1.70–1.95(m,2H), 2.50–3.55(m,8H), 4.05–4.18(m,1H), 7.10–7.48(m,25H)

7. A mixture of iso-valeryl chloride (0.05 ml), compound 10 (0.25 g) and triethylamine (0.11 ml) in dichloromethane (10 ml) was stirred at ambient temperature under an argon atmosphere for 3 h. The reaction was applied directly to a silica chromatography column which was eluted with ethyl acetate/iso-hexane(15:85), followed by (17:83), then (20:80) to give the desired starting material (compound 12a) as a white solid (0.292 g).

NMR (CDCl$_3$) δ:0.60+0.70+0.82(d dd,d, 6H), 1.05–1.25 (m,1H), 1.30+1.33+1.36(s,s,s, 9H), 1.55–4.445(m, 13H), 7.05–7.50(m, 25H)

EXAMPLE 2

2-(3-pyridyl)-N-(2,2-diphenyl-ethyl)-N-(cis)-3-sulfanylpyrrolidin-2-ylmethyl)acetamide (compound 14(b))

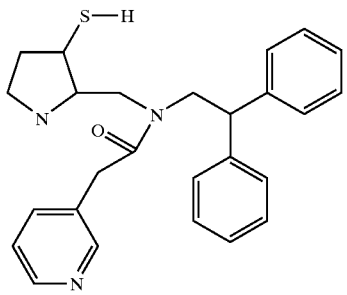

Compound 14(b) was prepared by a similar method to that described for preparation of compound 14(a) in Example 1.

NMR (CDCl$_3$) δ:2.10–2.25(m,1H), 2.35–2.55(m,1H), 3.15–3.53(m,4H), 3.55–3.95(m,3H), 4.00–4.25(m,1H), 4.30–4.55(m,3H), 7.10–7.50(m,12H), 7.55–7.75(m,1H), 8.07–8.20(m,1H), 8.38–8.55(m,1H), 8.70(s,1H), 9.38–9.60 (m,1H), 10.25–10.43(br.s,1H). Micro Analysis: % Theory C, 58.8; H, 6.45; N, 7.91. (2.0 HCl, 1.5 H2O) % Found C, 58.6; H, 6.10; N, 7.70.

The starting material, 2-(3-pyridyl)-N-(2,2-diphenyl-ethyl)-N(cis)-1-BOC-3-tritylsulfanylpyrrolidin-2-ylmethyl) acetamide (compound 12(b)), was prepared as follows:

A mixture of HOBT (0.076 g), EDC(0.103 g), 4-methylmorpholine (0.23 ml) and compound 10 (see Example 1; 0.269 g) and 3-pyridylacetic acid (0.093 g) in dichloromethane (12 ml) was stirred at 5° C. for 15 minutes and then at ambient temperature for 20 h. The solution was then applied to a silica chromatography column which was eluted with ethyl acetate/iso-hexane (30:70), followed by (60:40), then (90:10) and ethyl acetate to give the compound 12b as a white solid (0.217 g).

NMR (CDCl$_3$) δ1.05–1.25(m,1H), 1.37(s,9H), 1.70–4.50 (m,12H), 7.05–7.55(m,27H), 7.78–8.50(m,2H)

EXAMPLE 3

6-Methoxy-1-oxido-N-(2,2-diphenylethyl)-N-((cis)-3-sulfanylpyrrolidin-2-ylmethyl)-pyridine-3-carboxamide (compound 14(c))

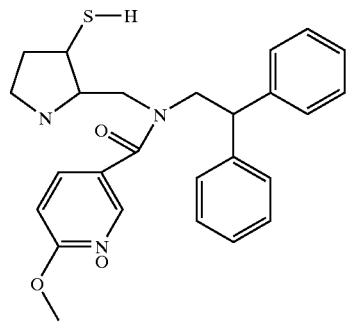

Compound 14(c) was prepared by a similar method to that described for the preparation of compound 14a in Example 1.

NMR (CDCl$_3$) δ1.15–1.35(m,1H), 1.88–2.03(m,1H), 2.21(d,1H), 2.28–2.50(m,1H), 3.00–3.20(m,1H), 3.20–3.37 (m,1H), 3.42–3.55(m,1H), 3.69(d,1H), 3.80–3.98(m,1H), 4.05(s,3H), 4.20–4.40(m,3H), 6.58(d,1H), 7.08–7.36(m, 11H), 8.11(s,1H), 9.10(br.s,1H), 10.8(br.s,1H) Micro Analysis: % Theory C, 60.0; H, 6.59; N, 8.08. (1.0 HCl, 1.0 H2O) % Found C, 59.6; H, 6.00; N, 7.80.

The starting material, 6-methoxy-1-oxido-N-(2,2-diphenyl-ethyl)-N-((cis)-1-BOC-3-tritylsulfanylpyrrolidin-2-ylmethyl)pyridine-3-carboxamide (compound 12(c)), was prepared from compound 10 (see Example 1) using the method described for compound 12(b) (in Example 2) using appropiate intermediates.

NMR (CDCl$_3$) δ: 0.75–1.00(m,1H), 1.10–1.25(m,1H), 1.25–1.45(m,9H), 1.90–3.75(m,8H), 3.90–4.15(m,3H), 4.20–4.90(m,1H), 6.30–6.55(m,1H), 6.60–7.50(m,27H)

EXAMPLE 4 a) N-(naphth-1-yl-ethyl)-N-((cis)-3-sulfanylpyrrolidin-2yl-methyl)-thiazole-5-carboxamide (compound 15(a)); and
b) 6-Methoxy-1-oxido-N-(naphth-1-yl-ethyl)-N-((cis)-3-sulfanylpyrrolidin-2-ylmethyl)pyridine-3-carboxamide (compound 15(b))

15a

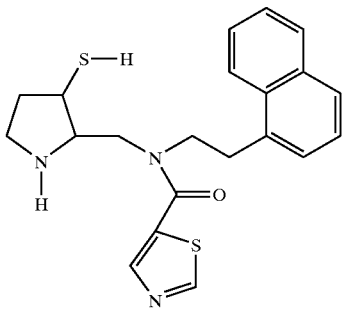

33

-continued

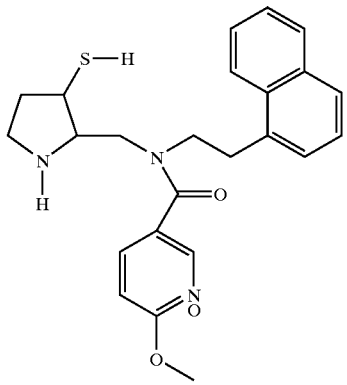

15b

Compound 15(a) and compound 15(b) were prepared by similar methods to those described for preparation of compound 14(a) in Example 1. The starting materials for compounds 15(a) and 15(b) were prepared from compound 9 (Example 1) using appropiate intermediates by similar procedures to those described in the synthesis of compounds 12(b) and 12(c) in Examples 2 and 3. In brief, the following reagents were used with respect to the steps numbered in Example 1.

Step 6: 1-naphthylamine/sodium triacetoxyborohydride/molecular sieve/−20°

Step 7: thiazole-5carboxylic acid (for 15(a)) or 6-methoxynicotinic acid N-oxide (for 15(b))/EDC/HOBT/4-methylmorpholine.

Characterising data:

Compound 15(a):

NMR (DMSO-d6) δ: 1.90–2.05(m,1H), 3.10–4.10(m, 11H), 7.30–7.95(m,8H), 8.12(s,1H), 9.08(s,1H), 9.30(br.s, 1H), 10.05(br.s,1H) Micro Analysis: % Theory C, 52.6; H, 5.47; N, 8.76. (2.0 HCl, 0.5 H2O) % Found C, 52.7; H, 5.3; N, 8.5.

Compound 15b:

NMR (CDCl$_3$) δ:2.30–2.45(m,2H), 2.90–4.15(m,13H), 6.27(d,1H), 6.90–8.05(m,10H), 9.20(br.s,1H), 10.60(br.s, 1H) Micro Analysis: % Theory C, 57.7; H, 6.36; N, 8.24. (1.0HCl, 1.5 H2O, 0.12Ethyl ether) % Found C, 57.8; H, 6.0; N, 8.2.

(cis)-1-BOC-N-(naphth-1-ethyl)-3-tritylsulfanyl-pyrrolidin-2-yl-methylamine which is the product (compound 11) of the reaction equivalent to step 6 (Example 1):

NMR (CDCl$_3$) δ 0.80–0.95(m, 1H), 1.34(s, 9H), 1.70–2.00(m, 1H), 2.50–3.65(m, 10H), 7.15–7.50(m, 19H), 7.65–7.73(m, 1H), 7.80–7.88(m, 1H), 8.00–8.12(m, 1H).

N-(naphth-1-yl-ethyl)-N-((cis)-1-BOC-3-tritylsulfanylpyrrolidin-2-yl-methyl)-thiazole-5-carboxamide (compound 13(a)) which is the product of the reaction equivalent to step 7 of Example 1 for synthesis of compound 15(a).

NMR (CDCl$_3$) δ: 0.80–0.95(m, 1H), 1.28(s, 9H), 1.80–4.40(m, 11H), 7.10–8.80(m, 24H).

6-Methoxy-1-oxido-N-(naphthyl-1-yl-ethyl)-N-((cis)-1-BOC-3-tritylsulfanylpyrrolidin-2-ylmethyl)pyridine-3-carboxamide (compound 13(b)) which is the product of the reaction equivalent to step 7 (Example 1) for compound 15(b):

NMR (CDCl$_3$) δ: 0.80–0.95(m, 1H), 1.30(s, 9H), 1.90–4.20(m, 14H), 5.95–6.10(m, 1H), 6.70–7.85(m, 24H).

34

EXAMPLE 5

(2S)-2-{2-Benzyl-5-[(cis)-3-sulfanylpyrrolidin-1-yl methylamino]benzoylamino}-4-methylsulfanylbutyric acid

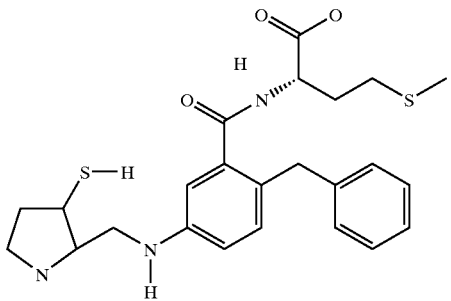

20

Compound 20 was prepared from compound 19 by standard procedures. In brief, 2N aqueous sodium hydroxide solution was added to a stirred solution of compound 19 in methanol at room temperature under argon. After 18 h the reaction mixture was concentrated to remove the Methanol. The resulting residues were dissolved in distilled water (2.0 mL) and acidified to pH3 with 2N HCl. The resulting solution was purified by reverse phase HPLC (Dynamax C18,8µ prepcolumn), eluting with a gradient of 0–40% Methanol/distilled water. Product fractions were concentrated and the desired end product purified by standard methods.

H$^1$NMR (DMSO-d$_6$+CD$_3$COOD) δ: 1.96(5H,m), 2.5 (5H.m+DMSO),3.18–3.48(3.5H,m), 3.75–4.04 (3.5H,m), 4.46(1H,q), 6.61(2H,m,Ar). 6.94–7.23(6H,m,Ar). MS (ESP+) m/z (M+H)$^+$ 474. Anal. Calcd for C$_{24}$H$_{31}$N$_3$S$_2$O$_3$.1.6TFA C, 49.8; H, 5.01; N, 6.4. Found C, 49.5; H, 5.1; N, 6.4.

The starting material was prepared as follows:

Isopropyl(2S)-2-{2-Benzyl-5-[(cis)-3-sulfanyl-pyrrolidin-2-ylmethyl-amino]benzoylamino}-4-methylsulfanylbutyrate (compound 19) was prepared form compound 18 using a similar procedure to that of Example 1, step 1

Isopropyl (2S)-2-{2-benzyl-5-[(cis)-3-tritylsulfanylpyrrolidin-2-ylmethylamino]benzoylamino}-4-methylsulfanylbutyrate (compound 18) was prepared by reacting compound 9 (Example 1) with isopropyl (2 S)-2-(5-amino-2-benzylbenzoylamino)-4-methylsulfanyl butyrate (compound 17) according to standard procedures. In brief, a solution containing compounds 9 and 17 in isopropyl alcohol was treated with powdered 4 Å molecular sieves and the resulting suspension was stirred at room temperature for 1 h. Acetic acid and sodium cyanoborohydride were then added and the reaction mixture was left to stir for 18 h at room temperature. The reaction mixture was then partitioned between ethyl acetate(50 mL) and saturated sodium hydrogen sulphate(aq) (50 mL). The aqueous phase was then washed with ethyl acetate (50 mL) and the combined organics dried over MgSO$_4$, filtered and concentrated to a colourless gum. This was then purified by flash chromatography on Silica (Varian Mega Bond Elut Column) eluting a gradient of 25–40% Ethyl acetate/i-hexane to give compound 18.

Compound 17 was prepared as follows:

A solution of methyl(2S)-2-(2-benzyl-5-nitro-benzoylamino)-4-methylsulfanyl- butyrate compound 34(d) (25.24 g, 62.78 mmol) in methanol (500 mL) was treated with 2N aqueous sodium hydroxide solution (35 mL, 70 mmol). The resulting solution was then evaporated to dryness and the solids partitioned between ethyl ether (200 mL) and water (500 mL). The aqueous material was then acidified to pH2 with 2N HCl and extracted with ethyl acetate (2×250 mL). The combined organics were washed with water(2×100 mL), brine(100 mL), filtered through phase separating paper and evaporated to give (2S)-2-(2-benzyl-5-nitro-benzoylamino)-4-methylsulfanyl- butyric acid (compound 36(a)) as a white solid, 23.57 g(96.8%).

$^1$H NMR (DMSO-d$_6$,300 MHz) δ: d1.8–2.2(5H,m); 2.3–2.6(2H+DMSO,m); 4.1–4.3(2H,m);4.4–4.6(1H,m); 7.1–7.3(5H,m);7.4–7.6(1H,m);8.1–8.3(2H,m); 8.9–9.0(1H, m,NHCO) MS (ESP–) m/z 387(M–H)$^-$.

Sulphuryl chloride (5.0 mL, 62 mmol) was added to a stirred suspension of compound 36a (19.2 g, 50 mmol) in IPA (500 mL). The resulting mixture was then heated at reflux for 18 hrs. The reaction mixture was then evaporated to ⅕ volume and partitioned between ethyl acetate (1 L) and saturated aqueous sodium hydrogen sulphate (500 mL).The organics were then washed with water (200 mL), brine (200 mL), filtered through phase separating paper and evaporated to give isopropyl (2S)-2-(2-benzyl-5-nitro-benzoylamino)-4-methylsulfanyl- butyrate (compound 36(b)) as a white solid, 21.25 g(100%).

$^1$H NMR (DMSO-d$_6$,300 MH$_z$) δ: 1.0–1.3(6Hm);1.8–2.2 (5H,m); 2.3–2.6(2H+DMSO,m);4.1–4.3(2H,m);4.4–4.6 (1H,m);4.8–5.0(1H,m);7.1–7.3(5H,m); 7.4–7.6(1H,m) ;8.1–8.3(2H,m);9.0(1H,m,NHCO) MS (ESP+) m/z 431(M+H)$^+$.

SnCl$_2$.2H2O (2.5 g, 11.08 mmol) was added to a stirred solution of compound 36(b) (2.24 mmol) in ethyl acetate(50 mL) and the resulting mixture heated at reflux for 18 hrs. The reaction mixture was cooled to ambient temperature and treated with 0.880 SG NH$_3$(aq) dropwise to pH8. The resulting precipitate was removed by filtration through diatomaceous earth. The filtrates were then evaporated and purified by chromatography (Mega Bond Elut,Silica), eluting with dichloromethane and then 50% ethyl acetate/i-hexane to give the desired aniline compound (17).

EXAMPLE 6

(2S)-2-{2-Benzyl-4-[(cis)-3-sulfanyl-pyrrolidin-2-ylmethylamino]benzoylamino}-4-methylsulfanylbutyric acid

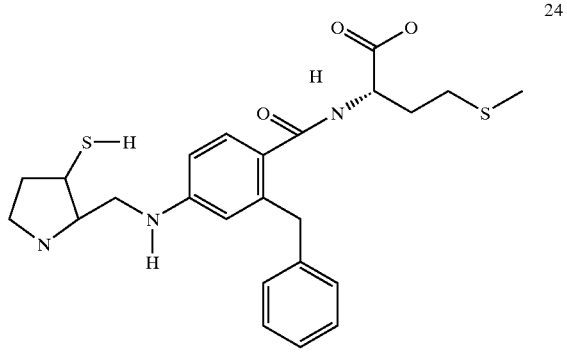

24

Compound 24 was prepared from compound 9 (Example 1) and methyl (2S)-2- (4-amino- 2-benzyl- benzoylamino)-4-methylsulfanyl- butyrate (compound 21) according to procedures outlined in Example 5.

H$^1$NMR (DMSO-d$_6$+CD$_3$COOD) δ: 1.98(5H,m), 2.48 (5H,m),3.18–3.46(3.5H,m), 3.75(1H,m), 3.9–4.2(2.5H,m), 4.43(1H,m), 6.46(2H.m.Ar), 7.04–7.34(6H,m,). MS (ESP+) m/z (M+H)+ 474. Microanalysis, calculated for C24H31N3S2O3.1.55TFA: C, 50.0; H, 5.04; N, 6.46. Found C, 49.9; H, 5.1; N, 6.4.

Compound 21 used in the preparation of compound 24 was prepared as follows. Sodium dichromate dihydrate (151 gm) was added to glacial acetic acid (575 ml) followed by 2-bromo-4-nitro-toluene (49.7 gm). To this solution was added dropwise sulphuric acid (175 ml) at such a rate to maintain the temperature between. 75–85° C. This mixture was heated to 100–110° C. for 3 h cooled to 50° C. and poured onto ice (1 litre). The aqueous phase was extracted with ethyl acetate, the organic layer back extracted with Aqueous sodium hydroxide solution and the resulting basic aqueous layer acidified with concentrated hydrochloric acid. The precipitated solid was filtered, washed with water and air dried to give 15.72 gm (28%) of 2-bromo-4-nitro-benzoic acid (compound 26) as a white solid.

NMR H$^1$NMR (CDCl$_3$) δ: 7.42 (1H,d),8.08 (1H,q),8.42 (1H,d)

Compound 26 in methanol was treated with SO$_2$Cl$_2$ and the resulting solution heated at reflux for18 h. The reaction mixture was then evaporated, pre-absorbed on silica (Merck, 9385) and purified by chromatography, eluting with 10% ethyl acetate/i-hexane. Appropriate fractions were combined and evaporated to give methyl 2-bromo-4-nitro-benzoate (compound 27).

A solution of benzyl bromide (2.0 mL, 17.3 mmol) in THF (10 mL) was added dropwise at 0° C. to a stirred suspension of zinc dust (1.7 g, 26 mmol) in THF (10 mL) which had been activated according to the method described by Knochel (J.O.C. 53, 2392, 1988). The mixture was left to warm to ambient temperature and stir for 3 h. An aliquot (6.5 mmol) of the supernatent containing the benzyl zinc reagent was then added to a stirred solution of compound 27 (3.85 mmol) and Pd(dba)$_3$ (0.0385 mmol) in THF (10 mL) at ambient temperature under argon. After 1 hr a second aliquot (6.5 mmol) of the benzyl zinc reagent was added. The resulting black reaction mixture was quenched with 2N HCl (250 mL) and extracted with Ethyl acetate (2×100 mL). The combined organics were washed with water (50 mL) and brine (50 mL), filtered through phase separating paper and evaporated to an orange gum. This was purified by chromatography on silica (Merck, 9385) eluting with 10% ethyl acetate/i-hexane to give methyl 2-benzyl-4-nitro-benzoic acid (compound 28).

2N Aqueous sodium hydroxide solution (2.0 mL, 4 mmol) was added to a solution of compound (28) (2.06 mmol) in methanol (10 mL) at ambient temperature. After 2 hrs the reaction mixture was evaporated to remove the methanol and then partitioned between ethyl ether (20 mL) and 2N aqueous sodium hydroxide solution (20 mL). The aqueous phase was acidified to pH⅔ with 2N HCl and extracted with ethyl acetate(3×20 mL). The combined organics were washed with water (20 mL) and brine (20 mL), filtered through phase separating paper and evaporated to yield 2-benzyl-4nitrobenzoic acid (compound 29).

Compound 29 (2.45 mmol) was coupled with L-methionine methyl ester hydrochloride (540 mg, 2.7 mmol) to give methyl 2-[(2-benzyl-4-nitro-benzoyl)amino]-4-methylsulfanyl-butyrate (compound 30).

$SnCl_2.2H_2O$ (2.5 g, 11.08 mmol) was added to a stirred solution of compound 30 (2.24 mmol) in ethyl acetate(50 mL) and the resulting mixture heated at reflux for 18 h. The reaction mixture was cooled to ambient temperature and treated with 0.880 SG $NH_3$(aq) dropwise to pH8. The resulting precipitate was removed by filtration through diatomaceous earth (Celite®)(545). The filtrates were then evaporated and purified by chromatography (Mega Bond Elut,Silica), eluting with dichloromethane and then 50% ethyl acetate/i-hexane to give the desired compound 21.

EXAMPLE 7

(2S)-2-(2-methoxy-ethyl)-1-((cis)-3-sulfanyl-pyrrolidin-2-ylmethyl)-4-naphthoyl-piperazine

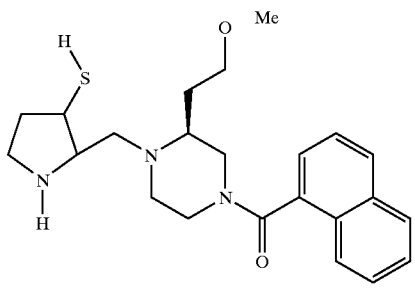

(32)

Compound 32 was synthesised from starting material (2S)-2-(2-methoxy-ethyl)-1-[cis]-1-BOC-3-tritylsulfanyl-pyrrolidin-2-ylmethyl)-4-naphthoyl-piperazine (compound 31) using a similar method to that of Example 1, step 1.

NMR (CDCl$_3$) δ 1.70–4.90(m, 24H), 7.35–8.00(m, 7H), 9.40–10.30(br.s, 1H), 10.50–11.80(br.s,1H). Micro Analysis: % Theory C, 54.0; H, 7.20; N, 8.01. (2.0HCl, 1.5H2O, 0.15 ethyl ether) % Found C, 54.3; H, 7.00; N, 8.00.

The starting material was prepared as follows. Compound 31 was synthesised from compound 9 (see Example 1) and (3S)-3-(2-methoxy-ethyl)-1-naphthoyl-piperazine (compound 16) by the method described in Example 1, step 6, for the preparation of compound 10. Compound 16 was prepared using analogous methods to those described in International Patent Application WO 95/00497 (Merck; Graham et al); see compound VIII, Scheme 2 and Example 7, Step E therein substituting naphthoic acid in lieu of 2,3-dimethylbenzoic acid.

NMR, compound 31, (CDCl$_3$) δ: 0.80–1.20(m, 1H), 1.30–1.43(m, 9H), 1.75–3.75(m, 20H), 3.95–4.55(m, 1H), 7.15–7.95(m, 22H).

EXAMPLE 8

The compounds in the following table were prepared from the appropriate tritylsulfanyl compounds using a similar method to that described in Example 1, paragraph 1.

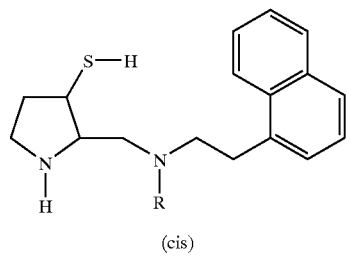

(cis)

Compound No. R
15c isovaleryl
15d 3-pyridylacetyl
15e 1-oxido-6-methoxypyridin-3-ylcarbonyl
15f thiazol-5-ylcarbonyl
Characterising data:
Compound 15(c):
  NMR (CDCl$_3$) δ: 0.75(t, 6H), 1.15–1.38(m, 1H), 1.50–1.80(m, 3H), 1.90–2.15(m, 1H), 2.32–2.52(m, 1H), 2.75–2.97(m, 1H), 3.00–3.26(m, 1H), 3.26–4.00(m, 8H), 7.25–8.03(m, 7H), 8.80–9.20(br.s, 1H), 11.2–11.7(br.s, 1H). Micro Analysis: % Theory C, 64.90; H, 7.68; N, 6.88; S,7.88. (1.0 HCl) % Found C, 65.20; H, 7.50; N, 6.90; S,7.90.
Compound 15(d):
  NMR (DMSOd$_6$) δ: 1.75–2.00(m, 1H), 2.30–2.60(m, 1H), 2.90–4.50(m, 12H), 7.40–7.65(m, 4H), 7.75–8.00(m, 3H), 8.15–8.30(m, 2H), 8.65–8.90(m, 3H), 9.90–10.40(m, 1H), Micro Analysis: % Theory C, 56.00; H, 6.46; N, 8.17; S,6.23. (2.0 HCl, 2.0H, $_2$O) % Found C, 55.70; H, 6.30; N, 8.20. S,6.00.
Compound 15(e):
  NMR (CDCl$_3$) δ: 1.10–1.40(m, 1H), 1.80–2.12(m, 2H), 2.40–2.60(m, 1H), 2.96–3.20(m, 1H), 3.20–3.45(m, 4H), 3.55–3.72(m, 1H), 3.78–4.07(m, 4H), 4.13–4.30(m, 1H), 6.25(d, 1H), 6.92(d, 1H), 7.15–7.89(m, 8H), 8.92–9.20(br.s, 1H), 10.6–10.8(br.s, 1H). Micro Analysis: % Theory C, 58.20; H, 6.18; N, 8.48; S,6.47. (1.0HCl, 1.20H2O) % Found C, 57.80; H, 5.80; N, 8.50; S6.50.
Compound 15(f):
  NMR (DMSO-d$_6$) δ: 1.80–2.00(m, 1H), 235–2.55(m, 1H), 3.05–4.05(m, 10H), 7.28–7.54(m, 5H), 7.74–7.94(m, 3H), 8.13(s, 1H), 9.10(s, 2H), 9.80–10.00(br.s,1H). Micro Analysis: % Theory C, 53.60; H, 5.36; N, 8.93; S,13.60. (2.0 HCl) % Found C, 54.00; H, 5.50; N, 9.00; S,13.30.
The starting materials were prepared as follows:
Compound 13(c) was prepared from compound 7 via trans-1-BOC-3-tritylsulfanylpyrrolidin-2carbaldehyde (compound 9(a)) and trans-N-(naphth-1-ylethyl)-1-BOC-3-tritylsulfanylpyrrolidin-2-ylmethylamide and (compound 11(a)) using a similar method to that described for the preparation of compound 12(a) but using 1-naphthylethylamine instead of 2.2-diphenylethylamine in paragraph 6.

Characterising data:
Compound 7:
NMR (CDCl₃) δ: 1.05–1.35(m, 1H), 1.42+1.44(s,s, 9H), 1.50–1.70(m, 1H), 2.77–2.94(m, 1H), 3.17+3.18(s,s, 3H), 3.30–3.56(m, 2H), 3.73+3.85(s,s, 3H), 4.60–4.95(m, 1H), 7.15–7.55(m, 15H).
Compound 9(a):
NMR (CDCl₃) δ 1.33+1.37(s,s, 9H), 1.60–2.08(m, 2H), 3.00–3.20(m, 2H), 3.35–3.68(m, 2H), 7.20–7.55(m, 15H), 9.42+9.54(s,s, 1H).
Compound 11(a):
NMR (CDCl₃) δ 1.15–1.30(m, 1H), 1.43(s, 9H), 1.65–1.80(m, 1h), 2.40–2.57(m, 1H), 2.83–2.92(m, 3H), 3.05–3.20(m, 3H), 3.35–3.95(m, 3H), 7.13–8.05(m, 22H).
Compound 13(c):
NMR (CDCl₃) δ 0.60–1.00(m, 6H), 1.15–1.35(m, 1H), 1.40–1.47(m, 9H), 1.50–2.30(m, 4H), 2.45–4.1 5(m, 10H), 7.10–8.30(m, 22H).

Compounds 13(d) to 13(f) were prepared from compound 11(a) by the method described in the preparation of compound 15(a) (Example 4) using the appropriate "acid".
Characterising data:
Compound 13(d):
NMR (CDCl₃) δ: 1.15–1.33(m, 1H), 1.40–1.53(m, 9H), 1.85–2.15(m, 1H), 2.50–4.25(m, 12H), 6.85–8.55(m, 26H).
Compound 13(e):
NMR (CDCl₃) δ: 1.10–1.30(m, 1H), 1.43(s, 9H), 1.60–4.10(m, 14H), 6.00–6.40(m, 1H), 6.60–6.75(m, 1H), 6.90–7.90(m, 23H)
Compound 13(f):
NMR (CDCl₃) δ: 1.05–1.30(m,1H), 1.43(s, 9H), 1.70–4.20(m, 11H), 7.10–7.90(m, 23H), 8.57–8.80(m, 1H).

EXAMPLE 9

Methyl (2S)-2-[2-phenyl-5-(trans-3-sulfanylpyrrolidin-2-ylmethylamino)benzoylamino]-4-methylsulfanylbutyrate (Compound 37)

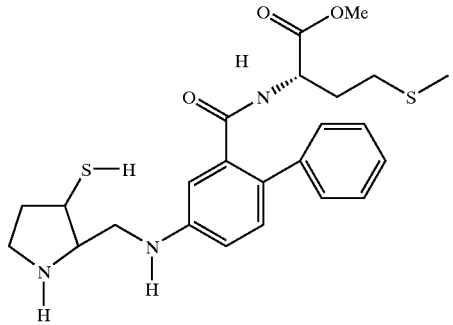

Methyl (2S)-2-[2-phenyl-5-(trans-3-sulfanylpyrrolidin-2-ylmethylamino)benzoylamino]-4-methylsulfanylbutyrate (compound 37) was prepared from methyl (2S)-2-[2-phenyl-5-(trans-3-tritylsufanylpyrrolidn-2-ylmethylamino) benzoylamino]-4-methylsulfanylbutyrate (compound 33) by a similar method to that described in Example 1, step 1.
Compound 37:
NMR (DMSO-d₆) δ: 1.76–1.94(m, 3H), 1.97(s, 3H), 2.10–2.30(m, 2H), 2.35–2.50(m, 1H), 3.13–3.58(m, 7H), 3.61(s, 3H), 4.30–4.39(m, 1H), 6.70(d, 1H), 6.79(dd, 1H), 7.15–7.30(m, 6H), 8.53(d, 1H), 9.42(br.s, 1H), 9.84(br.s, 1H). Micro Analysis: % Theory C, 51.70; H, 6.18; N, 7.54; S,11.50. (2.0 HCl, 0.6H2O) % Found C, 51.80; H, 5.90; N, 7.90; S, 11.60.

Compound 33 was prepared from compound 9(a) following the procedure described in the preparation of compound 18 (from Example 5) using the appropriate "aniline", methanol as solvent and employing 3 Å powdered sieves.

Compound 33:

NMR[(DMSO-d6) δ: 0.80–0.95(m, 1H), 1.38–1.45(m, 9H), 1.70–1.92(m, 3H), 1.97(s, 3H), 2.10–2.30(m, 2H), 2.70–2.86(m, 1H), 2.95–3.22(m, 4H), 3.60–3.65(m, 3H), 3.87–3.95(m, 1H), 4.30–4.43(m, 1H), 6.02(br.s, 1H), 6.60–6.78(m, 2H), 7.05–7.37(m, 21H), 8.30–8.50(m, 1H).

EXAMPLE 10

Methyl (2S)-2-[2-benzyl-4-((trans)-3-sulfanylpyrrolidin-2-ylmethylamino)benzoylamino]-4-methylsulfanylbutyrate (Compound 38)

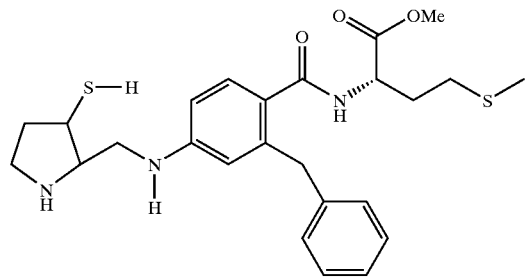

Methyl (2S)-2-[2-benzyl-4-((trans)-3-sulfonylpyrrolidin-2-ylmethylamino)benzoylamino]-4-methylsulfanylbutyrate (compound 38) was prepared from methyl (2S)-2-[2-benzyl-4-(trans-1-tertbutoxycarbonyl-3-tritylsulfanylpyrrolidin-2-ylmethylamino)benzoylamino]-4-methylsulfanylbutyrate using a similar method to that described in Example 1, step 1.

Compound 38:

NMR (DMSO-d₆) δ: 1.76–2.01(m, 3H), 2.03(s, 3H), 2.30–2.50(m, 2H), 3.10–3.55(m, 7H), 3.61(s, 3H), 3.99–4.17(m, 2H), 4.43–4.53(m, 1H), 6.49–6.54(m, 2H), 7.05–7.30(m, 6H), 8.39(d, 1H), 9.35(br.s, 1H), 9.79(br.s, 1H). Micro Analysis: % Theory C, 53.60; H, 6.29; N, 7.50; S,11.44. (2.0 HCl) % Found C, 53.40; H, 6.70; N, 7.60; S,11.40.

Compound 34 was prepared from compound 9(a) and the appropriate aniline using a similar method to that used to prepare compound 18 in Example 5.

Compound 34:

NMR (DMSO-d₆) δ: 0.73–0.90(m, 1H), 1.39–1.45(m, 9H), 1.62–1.75(m, 1H), 1.93–2.04(m, 2H), 2.05(s, 3H), 2.63–2.78(m, 1H), 2.88–3.30(m, 5H), 3.63(s, 3H), 3.85–4.27(m, 4H), 4,47–4.57(m, 1H), 6.00–6.09(br.s, 1H), 6.30–6.60(m, 2H), 7.08–7.32(m, 21H), 8.33–8.40(m, 1H).

EXAMPLE 11

(2S)-2-[2-Benzyl-5-((trans)-3-sulfanylpyrrolidin-2-ylmethylamino)benzoylamino]-4-methylsulfanylbutyric acid (compound 41) and
(2S)-2-[2-phenethyl-5-((trans)-3-sulfanylpyrrolidin-2-ylmethylamino)benzoylamino]-4-methylsulfanylbutyric acid (Compound 42)

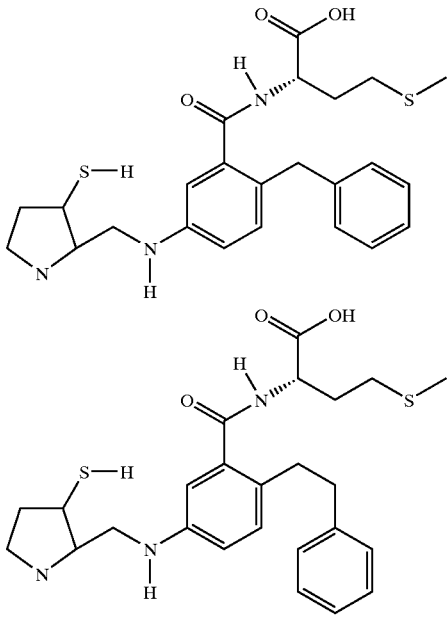

(2S)-2-[2-Benzyl-5-((tans)-3-sulfanylpyrrolidin-2-ylmethylamino)benzoylamino]-4-methylsulfanylbutyric acid (compound 41) and (2S)-2-[2-phenethyl-5-(trans-3-sulfanylpyrrolidin-2-ylmethylamino)benzoylamino]-4-methylsulfanylbutyric acid (compound 42) were prepared from the appropriate methyl ester (compounds 39 and 40 respectively) using a similar method to that used to prepare compound 27 (Example 6).

Compound 41:
NMR (DMSO-$d_6$) δ: 1.80–2.02(m, 3H), 2.02(s, 3H), 2.25–2.42(m, 2H), 3.10–3.75(m, 7H), 3.82–4.02(m, 2H), 4.39–4.47(m, 1H), 6.60–6.68(m, 2H), 6.95(d, 1H), 7.05–7.22(m, 5H), 8.48–8.55(m, 1H), 9.60(br.s, 1H), 9.93 (br,s, 1H). Micro Analysis: % Theory C, 47.60; HS.50; N, 6.95. (2.00HCl, 1.00NaCl) % Found C, 47.3; H, 5.10; N, 6.70.

Compound 42:
NMR (DMSO-$d_6$) δ: 1.75–2.00(m, 3H), 2.00(s, 3H), 2.30–2.90(m, 6H), 3.05–3.57(m, 7H), 4.43–4.53(m, 1H), 6.62–6.70(m, 2H), 7.00(d, 1H), 7.10–7.27(m, 5H), 8.50(d, 1H), 9.35(br.s, 1H), 9.78(br.s, 1H) Micro Analysis: % Theory C, 52.20; H, 6.13; N, 7.31. (2.00HCl, 0.25NaCl) % Found C, 52.20; H, 6.00; N, 7.10.

Compounds 39 and 40 were prepared from compound 9(a) via the trityl-protected sulfanylcompounds (compound 35 and 36 respectively) using a similar method to that used to prepare compound 37 (Example 10).

Compound 35:
NMR (DMSO-$d_6$) δ 0.85–0.97(m, 1H), 1.35–1.45(m, 9H), 1.67–1.83(m, 1H), 1.90–2.05(m, 2H), 2.03(s, 3H), 2.64–2.80(m, 1H), 2.92–3.32(m, 5H), 3.63(s, 3H), 3.82–4.05(m, 4H), 4.45–4.57(m, 1H), 5.63–5.75(br.s, 1H), 6.50–6.62(m, 2H), 6.83–6.93(m, 1H), 7.07–7.33(m, 20H), 8.53–8.59(m, 1H).

Compound 39:
NMR (DMSO-$d_6$) δ 1.75–2.03(m, 3H), 2.03(s, 3H), 2.30–2.50(m, 2H), 3.07–3.58(m, 7H), 3.60(s, 3H), 3.83–4.00(m, 2H), 4.42–4.58(m, 1H), 6.60–6.70(m, 2H), 6.90–7.24(m, 6H), 8.60–8.70(m, 1H), 9.35(br.s, 1H), 9.75 (br.s, 1H). Micro Analysis: % Theory C, 52.30; H, 6.41; N, 7.32; S,11.17. (2.00HCl, 0.75H2O) % Found C, 52.40; H, 6.40; N, 7.50;S,11.10.

Compound 36:
NMR (DMSO-$d_6$) δ: 0.83–0.93(m, 1 H), 1.38–1.45(m, 9H), 1.68–1.85(m, 1H), 1.97–2.07(m, 5H), 2.50–3.23(m, 1 1H), 3.61(s, 3H), 3.83–4.03(m, 1H), 4.53–4.61(m, 1H), 5.67(br.s, 1H), 6.50–6.63(m, 2H), 6.90–6.99(m, 1H), 7.10–7.35(m, 20H), 8.55–8.60(m, 1H)

Compound 40:
NMR (DMSO-d6) δ: 1.75–2.06(m, 3H), 2.03(s, 3H), 2.34–2.92(m, 6H), 3.10–3.57(m, 7H), 3.60(s, 3H), 4.50–4.60(m, 1H), 6.63–6.70(m, 2H), 7.00–7.28(m, 6H), 8.68(d, 1H), 9.38(br.s, 1H), 9.80(br.s,1H). Micro Analysis: % Theory C, 53.5; H, 6.56; N, 7.20; S,10.99. (2.00HCl, 0.50 H2O) % Found C, 53.5; H, 6.30; N, 7.20; S,10.90.

Methyl(2S)-2-(2-phenethyl-5-aminobenzoylamino)-4-methylsulfanylbutyrate (compound 79), used in the preparation of compound 36 was synthesised as follows;

A mixture of methyl 2-bromo-5-nitrobenzoate (10 g) phenyl acetylene (4.2 ml), triethylamine (100 ml), cuprous iodide(0.4 g),dimethylformamide (200 ml) and bis-(triphenylphosphine)-palladium(II)chloride (1.35 g) was stirred at ambient temperature for 1 hour under an argon atmosphere. The solvents were removed under reduced pressure and the residue treated with 1N, hydrochloric acid (2 L) and then extracted with ethyl acetate (2×300 ml). The combined organic extracts were washed with saturated aequeous sodium bicarbonate solution (100 ml), water (3×100 ml) and brine (100 ml) filtered through phase separating paper and evaporated to dryness. The residue was purified by flash column chromatography on silica using ethyl acetate/hexane(gradient: 0 to 10%) as eluant to give methyl 2-(2-phenylethynyl)-5-nitrobenzoate (compound 76) as a yellow solid (9.98 g).

Compound 76:
NMR (CDCl$_3$) δ: 4.02(s, 3H), 7.38–7–44(m, 3H), 7.59–7.64(m, 2H), 7.80(d, 1H), 8.33(dd, 1H), 8.84(d, 1H).

A mixture of compound 76(9.4 g), 10% Pd/C (0.94 g) and ethyl acetate (1 L) was stirred under an hydrogen atmosphere at 1 bar pressure for 16 hours. The mixture was filtered through a pad of Celite and the filtrate evaporated under reduced pressure to give methyl 2-phenethyl-5-aminobenzoate (compound 77) as an oil(8.5 g).

Compound 77:
NMR (CDCl$_3$) δ: 2.80–2.88(m, 2H), 3.08–3.16(m, 2H), 3.86(s, 3H), 6.73(dd,1H), 6.98(d, 1H), 7.15–7.30(m, 6H).

A mixture of compound 77(8.5 g), 2N. aqueous sodium hydroxide (50 ml) and methanol (100 ml) was stirred at ambient temperature for 18 hours and then heated at reflux for 2 hours. The mixture was cooled and evaporated under reduced pressure. The product was redissolved in water (1 L) and washed with diethyl ether (250 ml). The aqueous solution was acidified to pH 5–6 with glacial acetic acid . The resulting precipitate was isolated by filtration and dried under vacuum at 60° C. to give a powder which was azeotroped with toluene (3×50 ml) and then dried under high vacuum to give 5-amino-2-phenethylbenzoic acid (compound 78) (8.0 g).

Compound 78:
NMR (DMSO-$d_6$) δ: 2.68–2.76(m, 2H), 2.94–3.00(m, 2H), 6.62(dd, 1H), 6.93(d, 1H), 7.05(d, 1H), 7.12–7.30(m, 5H).

A mixture of L-methionine methyl ester HCl. (12.41 g), compound 78(5 g), EDC (4.77 g) and DMAP (13.61 g) in dichloromethane (250 ml) was stirred at ambient temperature for 3 hours. The dichloromethane was evaporated under reduced pressure and the residue treated with 1M. aqueous citric acid solution (200 ml) and then extracted with ethyl acetate (2×100 ml). The combined organic extracts were washed with- saturated aqueous sodium bicarbonate (100 ml) dried and evaporated to dryness. The product was purified on a silica flash column using ethyl acetate/isohexane as eluant (50:50) to give compound 79 as a solid (6.73 g).

Compound 79:
NMR (DMSOd$_6$) δ: 1.96–2.16(m, 2H), 2.03(s, 3H), 2.45–2.60(m, 4H), 2.69–2.82(m, 2H), 3.60(s, 3H), 4.53(q, 1H), 5.04(s, 2H), 6.51–6.60(m, 2H), 6.85–91(d, 1H), 7.13–7.28(m, 5H), 8.59(d, 1H).

EXAMPLE 12

| Compound | R$^1$ | Position of R$^1$ on phenyl | R$^2$ | Position of R$^2$ containing substituent on phenyl |
|---|---|---|---|---|
| 47 | Ph— | 4 | Me | 3 |
| 48 | PhCH$_2$— | 4 | Me | 3 |
| 49 | PhCH$_2$CH$_2$— | 4 | Me | 3 |
| 50 | 4-F-PhCH$_2$CH$_2$ | 3 | Me | 4 |
| 51 | PhCH$_2$CH$_2$— | 4 | H | 3 |
| 52 | 4-F-PhCH$_2$CH$_2$— | 3 | H | 4 |

Compounds 51 and 52 were prepared from compounds 40 and 50 respectively using a similar method to that used to prepare compound 27 (Example 6). Compounds 47, 48, 49 and 50 were prepared by deprotecting the appropriate tritylsulfanyl compounds (compounds 43, 44, 45 and 46 respectively) using a similar method to that of Example 1, step 1.

Compound 47:
NMR (DMSOd$_6$) δ: 1.72–1.88(m, 3H), 1.97(s, 3H), 1.97–2.35(m, 3H), 3.13–3.57(m, 5H), 3.60(s, 3H), 3.65–3.86(m, 2H), 4.30–4.40(m, 1H), 6.70(d, 1H), 6.80(dd, 1H), 7.15–7.32(m, 6H, 8.47–8.53(m,1H), 9.43(br.s, 1H), 9.90(br.s, 1H). Micro Analysis: % Theory C, 51.70; H, 6.18; N, 7.54; S,11.50. (2.00HCl, 0.60 H2O) % Found C, 51.90; H, 6.10; N, 7.80; S,11.60.

Compound 48:
NMR (DMSO-d$_6$) δ: 1.90–2.05(m, 3H), 2.03(s, 3H), 2.35–2.53(m, 1H), 3.15–3.55(m, 6H), 3.62(s, 3H), 3.65–3.99(m, 4H), 4.43–4.53(m, 1H), 6.63–6.70(m, 2H), 6.97(d, 1H), 7.07–7.23(m,5H), 8.63–8.70(m, 1H), 9.39(br.s, 1H), 9.85(br.s, 1H). Micro Analysis: % Theory C, 51.89; H, 6.45; N, 7.26. (2.00 HCl, 1.00 H2O) % Found C, 51.60; H, 6.40; N, 7.20.

Compound 49:
NMR (DMSO-d$_6$) δ: 1.93–2.04(m, 6H), 2.35–2.92(m, 6H), 3.15–3.55(m, 5H), 3.60(s, 3H), 3.63–3.84(m, 2H), 4.50–4.60(m, 1H), 6.65–6.70(m, .2H), 6.99–7.30(m, 6H), 8.68(d, 1H), 9.41(br.s, 1H),9.90(br.s, 1H). Micro Analysis: % Theory C, 53.50; H, 6.56; N, 7.20; S,10.99. (2.00HCl, 0.5 H2O) % Found C, 53.30; H, 6.20; N, 7.20; S,10.90.

Compound 50:
NMR (DMSO-d$_6$)δ1.91–2.09(m, 2H), 2.04(s, 3H), 2.33–2.65(m, 4H), 2.65–3.10(m, 5H), 3.10–3.39(m, 2H), 3.49(s, 1H), 3.60(s, 3H), 3.71(m, 2H), 4.49(q, 1H), 5.88(br.s, 2H), 6.51(m, 2H), 7.05(m, 2H), 7.24(m, 3H), 8.39(d, 1H), 9.30–9.50(br.s, 1H), 9.95(br.s, 1H.). Micro Analysis: % Theory C, 51.98; H, 6.19; N, 7.00; S,10.68. (2 HCl, 0.45 H2O) % Found C, 51.60; H, 15.90; N, 7.40; S,10.60.

Compound 51:
NMR (DMSO-d$_6$) δ: 1.93–2.04(m, 6H), 2.35–2.87(m, 6H), 3.15–3.85(m, 7H), 4.42–4.53(m, 1H), 6.60–6.67(m, 2H), 7.00(d, 1H), 7.10–7.27(m, 5H), 8.47–8.55(m, 1H), 9.35(br.s, 1H), 9.80(br.s, 1H). Micro Analysis: % Theory C, 53.60; H, 6.30; N, 7.50. (2.00 HCl) % Found C, 53.50; H, 6.10; N, 7.40.

Compound 52:
NMR (DMSO-d$_6$) δ: 1.90–2.05(m, 2H), 2.00(s, 3H), 2.38–2.58(m, 4H), 2.69–3.05(m, 5H), 3.15–3.38(m, 2H), 3.43–3.51(m,1H), 3.69–3.75(m, 2H), 3.88–4.05(m, 1H), 4.38–4.49(q,1H), 6.46–6.58(d,2H), 7.06(m, 2H), 7.25(m, 3H), 8.25(d,1H), 9.4(br.s,1H), 9.95(br.s, 1H) Micro Analysis: % C, 50.86; H, 6.03; N, 7.12; S,10.86. (2HCl, 0.65 H2O) % C, 50.50; H, 5.70; N, 7.20; S,10.80.

The starting material was prepared as follows:
Compounds 43, 44, 45 and 46 were prepared by reacting compound 9 with the appropriate aniline using a similar method to that used to prepare compound 18 in Example 5.

Compound 43
NMR (DMSOd$_6$) δ: 1.20–1.35(m, 9H), 1.53–1.85(m, 3H), 1.95(s, 3H), 2.10–2.30(m, 3H), 2.50–3.20(m, 6H), 3.55–3.60(m, 3H), 4.25–4.37(m, 1H), 5.30–5.58(m, 1H), 6.55–6.67(m, 2H), 7.05(d, 1H), 7.17–7.44(m, 20H), 8.35–8.47(m, 1H).

Compound 44
NMR (DMSOd$_6$) δ: 1.17–1.33(m, 9H), 1.47–1.62(m,1H), 1.83–2.00(m, 3H), 2.00(s, 3H), 2.02–2.50(m, 2H), 2.60–3.30(m, 6H), 3.59(s, 3H), 3.80–3.95(m, 2H), 4.43–4.52(m, 1H), 4.97–5.27(m, 1H), 6.40–6.60(m, 2H), 6.84(d, 1H), 7.05–7.43(m, 20H), 8.47–8.57(m, 1H).

Compound 45:
NMR (DMSOd$_6$) δ: 0.83–0.95(m, 1H), 1.20–1.38(m, 9H), 1.46–1.62(m, 1H), 1.85–2.20(m, 6H), 2.45–3.27(m, 11H), 3.58(s, 3H), 4.45–4.55(m, 1H), 4.92–5.22(m, 1H), 6.40–6.63(m, 2H), 6.90(d, 1H), 7.10–7.43(m, 20H), 8.50–8.60(m, 1H).

Compound 46:
NMR (CDCl$_3$) δ: 1.41(s, 9H), 2.00–2.10(m, 1H), 2.08(s, 3H), 2.14–2.34(m, 2H), 2.47–2.63(m, 2H), 2.80–3.20(m, 8H), 3.20–3.50(m, 2H), 3.75(s, 3H), 4.13–4.21(m, 1H), 4.85(q, 1H), 5.23(br.s, 1H.), 6.15–6.35(m, 3H), 6.89–6.95(t, 2H), 7.13–7.33(m, 12H), 7.41–7.51(d, 6H).

The "aniline" (compound 62) used in the preparation of compound 46 was synthesised from methyl 2-(2-(4-fluorophenyl)ethynyl)-4-nitrobenzoate by standard hydrogenation to give methyl 2-(4-fluorophenethyl)-4-aminobenzoate (compound 60). Compound 60 was hydrolysed to the corresponding benzoic acid (compound 61).

Compound 61 was coupled with L-methionine methyl ester hydrochloride-using similar conditions to those described for the preparation of compound 79 (Example 11) to give compound 62

Compound 60:
NMR (CDCl$_3$) δ: 2.74(t, 2H), 3.03(m, 2H), 3.71(s, 3H), 5.80(s, 2H), 6.40(s, 2H), 7.04–7.12(m, 2H), 7.23–7.31(m, 2H), 7.64(dd, 1H).

Compound 61:
NMR (CDCl3) δ2.87(t, 2H), 3.21(t, 2H), 6.41 (s, 1H), 6.53(d, 1H), 6.91–7.00(m, 2H), 7.16–7.23(m, 2H), 8.00(d, 1H).

Compound 62:
NMR (CDCl3) δ2.00–2.1 1(m, 1H), 2.09(s, 3H), 2.20–2.32(m, 1H), 2.57(t, 2H) 2.85(t, 2H), 2.96–3.13(m, 2H), 3.71–4.00(m, 2H), 3.77(s, 3H), 4.85(q, 1H), 6.35(d, 1H), 6.43–6.52(m, 2H), 6.91–6.96(m, 2H), 7.11–7.17(m, 2H), 7.28–7.32(m, 1H).

EXAMPLE 13

(2S)-2-[2-(2(4-Fluorophenyl)ethynyl)-4-(cis-3-sulfanylpyrrolidin-2-ylmethylamino)benzoylamino]-4-methylsulfanylbutyric acid (Compound 59)

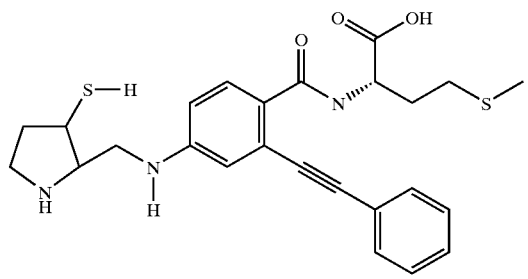

Compound 59 was prepared from the corresponding methyl ester (compound 58) using a similar method to that described for the preparation of compound 20 in Example 5.

Compound 59:
NMR (DMSO-d$_6$) δ: 1.91(s, 3H), 1.91–2.04(m, 1H), 2.16–2.31(m, 1H), 2.36–2.57(m, 2H), 2.57–2.73(m, 1H), 3.16–4.20(m, 9H), 4.53(q, 1H), 6.71–7.88(m, 7H), 8.36(d, 1H), 9.55(br.m, 1H), 9.85(br.m, 1H). Micro Analysis: % Theory C, 51.06; H, 5.40; N, 7.15; S,10.91. (2.00 HCl, 0.75 H2O) % Found C, 51.20; H, 5.40; N, 5.40; S,10.60.

The starting material was prepared as follows;

A mixture of compound 53 (from Example 12) (2.5 g), 2N aqueous sodium hydroxide (15 ml) and methanol (150 ml) was heated at reflux for 2 hours. The mixture was cooled and the methanol evaporated away. The residue was treated with 2N HCl (20 ml) and the mixture extracted with ethyl acetate (2×100 ml). The organic extracts were combined, dried and evaporated to dryness to give 2-[2-(4fluorophenyl)ethynyl]-4-nitrobenzoic acid (compound 54) (2.3 g).

Compound 54 was converted to methyl (2S)-2-{2-[2-(4-fluorophenyl)ethynyl]-4-nitrobenzoylamino}-4-methylsulfanylbutyrate (compound 55) using the coupling procedure described for the preparation of compound 79 (Example 11).

Compound 55:
NMR (CDCl$_3$) δ: 2.00(s, 3H), 2.10–2.20(m, 1H), 2.20–2.37(m, 1H), 2.48–2.64(m, 2H,), 3.76(s, 3H,), 4.96(q, 1H), 7.10–7.20(m, 2H), 7.63–7.68(m, 2H), 7.84–7.97(m, 1H), 8.20–8.29(m, 2H), 8.45(d, 1H).

A mixture of compound 55 (2 g), stannous chloride dihydrate(4.4 g) and ethyl acetate (150 ml) was stirred and heated at reflux for 2 hours. It was then cooled and treated dropwise with aequeous ammonia(0.880) to pH 9. The white precipitate formed was filtered and washed with more ethyl acetate (150 ml). The filtrate and washings were combined, dried and evaporated to dryness to give an oil which was purified by flash chromatography on silica using ethyl acetate/iso-hexane as eluant to give methyl (2S)-2-{2-[2-(4-fluorophenyl)ethynyl]-4-aminobenzoylamino}-4-methylsulfanylbutyrate as a yellow solid (compound 56) (1.1 g).

Compound 56:
NMR (CDCl$_3$) δ: 1.99(s, 3H), 2.05–2.12(m, 1H), 2.19–2.31(m, 1H), 2.44–2.76(m, 2H), 3.91(s, 3H), 4.00(s, 2H), 4.96(q, 1H), 6.67–6.72(m, 1H), 6.85(d, 1H), 7.05–7.16 (m, 2H), 7.57–7.62(m, 2H), 7.97(d, 1H), 8.05–8.12(m, 1H).

Compound 56 was reacted with compound 9 to give methyl (2S)-2-{2-[2-(4-fluorophenyl)ethynyl]-4-(1-tert-butoxycarbonyl-3-tritylsulfanylpyrrolidin-2-ylmethylamino)benzoylamino}-4-methylsulfanylbutyrate. (compound 57) using a similar method to that used to prepare compound 33.

Compound 57:
NMR (CDCl$_3$) δ: 1.40(s, 9H), 1.63–1.88(m, 1H), 1.96–2.08(m, 1H), 1.99(s, 3H), 2.16–2.32(m, 1H), 2.43–2.61(m, 2H), 2.80–3.55(m, 6H), 3.70(s, 3H), 4.24–4.45(m, 1H), 4.96(q. 1H), 5.45(br.s, 1H), 6.45–6.68(m, 2H), 7.08(t. 2H), 7.20–7.33(m, 10H), 7.48(d, 6H), 7.60(q, 2H), 7.96(d, 1H), 8.10(d, 1H).

Compound 57 was converted to compound 58 using a similar method to that described in Example 1, step 1.

Compound 58:
NMR (DMSO-d$_6$) δ: 1.72–2.96(m, 6H), 1.97(s, 3H), 3.19–3.96(m, 5H), 3.71(s, 3H), 4.00–4.24(m, 1H), 4.88(q, 1H), 6.60–7.88(m, 7H), 8.08(d, 1H), 9.91(br.s, 1H) Micro Analysis: % Theory C, 53.05; H, 5.48; N, 7.14; S,10.90. (2HCl) % Found C, 53.00; H, 5.60; N, 7.40; S11.00.

EXAMPLE 14

(2S)-2-[2-(4-Fluorophenethyl)-5-([2R,3R]-3-sulfanylpyrrolidin-2-ylmethylamino)benzoylamino]-4-methylsulfanylbutyric acid (Compound 73)

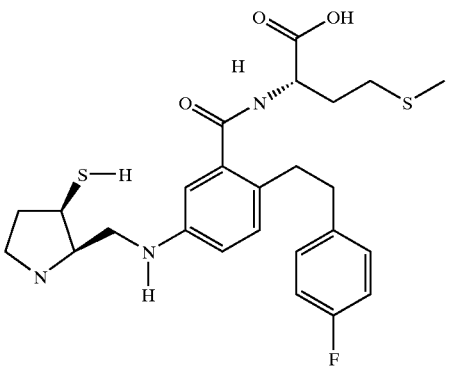

Compound 73 was prepared from the corresponding iso-propyl ester (compound 72) using a similar method to that of Example 5.

Compound 73:
NMR (DMSOd$_6$) δ 1.91–2.08(m, 2H), 2.02 (s, 3H), 2.31–2.52(m, 4H), 2.52–2.57(m, 1H), 2.65–2.85(m, 3H), 3.27–3.48(m,3H), 3.69–3.99(m, 5H), 4.47(m,1H), 6.63(s, 2H), 6.93–7.08 (m, 3H), 7.16–7.23(m, 2H), 8.48(d, 1H), 9.72(br.s, 1H). Micro Analysis: % Theory C, 49.56; H, 5.91; N, 6.94; S,10.59. (2.5HCl, 0.5 H$_2$O) % Found C, 49.90; H, 5.70; N, 6.90; S,10.90.

The starting material was prepared as follows:

A mixture of trans-3-hydroxy-L-proline (5 g), di-tert-butyl dicarbonate(9.15 g), sodium hydroxide(1.52 g), water (78 ml) and dioxan (80 ml) was stirred at 5° C. for 30 mins. and then at ambient temperature for 16 hours. The mixture was evaporated to a smaller volume (30 ml) and diluted with water (150 ml). The pH was adjusted to 2–3 with aqueous sodium bisulphate and saturated with sodium chloride. It was then extracted with ethyl acetate(3×100 ml), the extracts dried and the solution evaporated to dryness to give (2S, 3S)-1-(tert-butoxycarbonyl)-2-carboxy-3-hydroxypyrrolidine (compound 64) as a white solid (8.42 g).

Compound 64:

NMR (DMSOd$_6$) δ: 1.27(2s, 9H), 1.64 1.76(m, 2H), 3.24–3.45(m, 2H), 3.92(d, 1H), 4.20(br, 1H), 5.40(br, 1H), 12.6(br, 1H).

A mixture of compound 64 (8.42 g), N,O-dimethyl hydroxylamine HCl (10.66 g), DMAP (26.69 g), and EDC (10.47 g) in dichloromethane (500 ml) was stirred at ambient temperature for 16 hours. The reaction mixture was then applied directly to a silica flash column and eluted with ethyl acetate to give (2S,3S)-1-(tert-butoxycarbonyl)-3-hydroxy-2-(N-methoxy-N-methylcarbamoyl)pyrrolidine (compound 65) as a clear gum(7.6 g).

Compound 65:

NMR (CDCl$_3$) δ: 1.43(2s, 9H), 1.80–1.93(m, 1H), 2.07–2.34(m, 2H), 3.20(s, 3H), 3.53–3.72(m, 2H), 3.80(d, 3H), 4.36(br, 1H), 4.63(d, 1H).

Methane sulphonyl chloride (3.49 g) was added dropwise over 10 minutes to a mixture of compound 65 (7.6 g) and triethylamine (7.7 ml) in dichloromethane (350 ml) and cooled to 0° C. under an argon atmosphere. It was then stirred at 0° C. for another hour. The reation mixture was then applied directly to a silica flash column which was eluted with ethyl acetate to give (2S,3 S)-1-tert-butoxycarbonyl)-2(N-methoxy-N-methylcarbamoyl)-3-methansulfonyloxypyrrolidine (compound 66) as a gum (9.7 g).

Compound 66:

NMR (CDCl$_3$) δ: 1.44(2s, 9H), 2.08–2.40(m, 2H), 3.08(s, 3H), 3.23(s, 3H), 3.50–3.62(m, 1H), 3.70–3.88(m, 1H), 3.80–3.85(d, 3H), 4.92(d, 1H), 5.17(dd, 1H)

A solution of triphenylmethyl mercaptan (11.22 g) in DMF (150 ml) was added dropwise over 15 minutes to a suspension of sodium hydride (60% dispersion in mineral oil. 1.62. g. in DMF (100 ml) stirred under an argon atmosphere and cooled to 5° C. It was then stirred for a further 30 minutes. A solution of compound 66 (9.7 g) in DMF (50 ml) was then added and the reaction mixture allowed to warn to ambient temperature and stirred for a further 2 hours. It was then heated at 50° C. for 4 hours, cooled to ambient temperature and the DMF evaporated under reduced pressure. The residue was then treated with 1M. aqueous citric acid (200 ml) and extracted with ethyl acetate (3×100 ml). The extracts were combined, washed with brine (100 ml), dried and evaporated under reduced pressure. The product was purified by flash column chromatography, eluting with ethyl acetate/iso-hexane (50:50) to give (2R,3R)-1-(tert-butoxycarbonyl)-2(N-methoxy-N-methylcarbonyl)-3-tritylsulfanylpyrrolidine (compound 67) as a solid foam (1.3 g).

Compound 67:

NMR (CDCl$_3$) δ 0.91–1.01(m, 1H), 1.31(s, 9H), 2.00–2.10(m, 1H), 2.81–3.00(m, 2H), 3.30(s, 3H), 3.31–3.60(m, 1H), 3.70–4.00(d, 3H), 5.10(d, 1H), 7.11–7.30 (m, 10H), 7.50(d, 5H). Compound 67 was reduced to (2R,3R)-1-(tert-butylcarbonyl)-2-formyl-3-tritylsulfanylpyrrolidine (compound 68) with lithium aluminium hydride using a similar procedure to that described for the preparation of compound 9 in Example 1.

Compound 68:

NMR (CDCl$_3$) δ: 1.33(2s, 9H), 1.61–1.81(m, 1H), 1.93–2.08(m,1H),3.00–3.65(m, 4H), 7.21–7.35(m, 10H), 7.49(d, 5H), 9.47 (d, 1H).

Methyl 2-(4-fluorophenethyl)-5-(2R,3R)-1-(tert-butoxycarbonyl-3-tritylsulfanylpyrrolidin-2-yl)benzoate (compound 69) was prepared by reacting compound 68 with methyl 5-amino-2-(4-fluorophenethyl)benzoate (compound 75) under reductive amination conditions, similar to those described for the preparation of compound 17 in Example 5, but using methanol in place of isopropanol.

Compound 69:

NMR (CDCl$_3$) δ 1.40(s, 9H), 2.63–3.17 (m, 9H), 3.41–3.53 (m, 1H), 3.87(s, 3H), 6.49–6.65 (br.s, 1H), 6.88–7.00 (m, 3H), 7.00–7.07(m, 1H), 7.13–7.33 (m,12H), 7.48(d, 6H).

Standard base hydrolysis of compound 69 with sodium hydroxide gave the corresponding benzoic acid (compound 70).

Compound 70:

NMR (CDCl$_3$) δ: 1.41(s, 9H), 1.45–1.68(m, 7H), 2.79–2.96(m, 4H), 3.09–3.16(m, 3H), 6.91–6.96(m, 3H), 7.11–7.33(m, 12H) 7.47–7.53(m, 6H).

Compound 70 was coupled with L-methionine isopropyl ester in dichloromethane in the presence of EDC and DMAP to give isopropyl (2S)-2-[2-(4-fluorophenethyl)-5-((2R,3R)-1-(tert-butoxycarbonyl)-3-titylsulfanylpyrrolidin-2-ylmethylamino)benzoylamino]-4-methylsulfanylbutyrate (compound 71).

Compound 71:

NMR (CDCl$_3$) δ: 1.27(m, 6H), 1.49(2s, 9H),1.92–2.13(m, 1H), 2.05(s, 3H), 2.13–2.31(m,1H), 2.51–2.60(m, 1H), 2.78–2.99(m, 4H), 3.07–3.19(m, 1H),4.73–4.89(m, 1H), 5.00–5.13(m, 1H), 6.31–6.43(m, 1H), 6.43–6.64(m, 1H), 6.88–6.94(m, 3H), 7.09–7.16(m, 2H), 7.20–7.33(m, 10H), 7.45–7.51 (m, 5H).

Compound 71 was deprotected with TFA and triethylsilane to give isopropyl (2S)2-[2-(4-fluorophenethyl)-5-((2R, 3R)-3-sulfanypyrrolidin-2-yl)methylamino)benzoylamino]-4-methylsulfanylbutyrate (compound 72).

Compound 72:

NMR (DMSO-d$_6$) δ: 1.13(m, 6H), 1.91–2.04(m, 2H), 2.00(s, 3H), 2.51–2.62(m, 2H), 2.65–2.85(m, 41), 3.12–3.53 (m, 5H), 3.65–4.00(m, 2H), 4.45(q, 1H), 4.84–4.93(m, 1H), 5.60–5.92(br, 4H), 6.67(s, 2H), 6.96–7.07(m, 3H), 7.16–7.23(m, 2H), 8.61(d, 1H), 9.45(br.s, 1H), 9.92(br.s, 1H).

Compound 75 was synthesised as follows;

A mixture of methyl 2-bromo-5-nitrobenzoate (5 g), 4-fluorostyrene (3.5 g), tributylamine (0.39 g), bis-(triphenylphosphine)-palladium(II)chloride (0.3 g), sodium bicarbonate (2.65 g) and water (30 ml) was stirred and heated at reflux under an argon atmosphere for 1.5 hours. The reaction was then cooled, suspended in dichloromethane (200 ml) and passed through a pad of silica (chromatography grade) eluting with more dichloromethane The dichloromethane was then evaporated away and the residue treated with iso-hexane (200 ml) to give methyl 2-[2-(4-fluorophenyl)ethynyl]-5-nitrobenzoate (compound 74) as a yellow precipitate which was filtered and dried, (5.05 g).

Compound 74:

NMR (CDCl$_3$) δ: 3.99(s, 3H), 7.08(t, 2H), 7.15(d, 1H), 7.55(q, 2H), 7.88(d, 1H), 8.0(d, 1H), 8.32(2d, 1H), 8.8(d, 1H).

A mixture of compound 74 (29 g), 10% Pd/C (3 g), and ethyl acetate (400 ml) was stirred under an hydrogen atmosphere for 6 hours. The catalyst was removed by filtration and replaced by fresh catalyst (3 g). The hydrogenation was then continued for another 16 hours, the catalyst was again filtered off, the filtrate evaporated to dryness and the residue treated with iso-hexane to give a white precipitate which was isolated by filtration and dried to give compound 75 (23.5 g).

Compound 75:

NMR (CDCl$_3$) δ: 2.8(t, 2H), 3.1(t, 2H), 3.62(s, 2H), 3.88(s, 3H), 6.72(dd, 1H), 6.93(m, 3H), 7.13(m, 2H), 7.23(d, 1H).

EXAMPLE 15
Pharmaceutical compositions

The following illustrate representative pharmaceutical dosage forms of the invention as defined herein (the active ingredient being termed "Compound X"), for therapeutic or prophylactic use in humans:

| (a) | Tablet I | mg/tablet |
|---|---|---|
| | Compound X | 100 |
| | Lactose Ph.Eur | 182.75 |
| | Croscarmellose sodium | 12.0 |
| | Maize starch paste (5% w/v paste) | 2.25 |
| | Magnesium stearate | 3.0 |

| (b) | Tablet II | mg/tablet |
|---|---|---|
| | Compound X | 50 |
| | Lactose Ph.Eur | 223.75 |
| | Croscarmellose sodium | 6.0 |
| | Maize starch | 15.0 |
| | Polyvinylpyrrolidone (5% w/v paste) | 2.25 |
| | Magnesium stearate | 3.0 |

| (c) | Tablet III | mg/tablet |
|---|---|---|
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |

| (d) | Capsule | mg/capsule |
|---|---|---|
| | Compound X | 10 |
| | Lactose Ph.Eur | 488.5 |
| | Magnesium | 1.5 |

| (e) | Injection I | (50 mg/ml) |
|---|---|---|
| | Compound X | 5.0% w/v |
| | 1 M Sodium hydroxide solution | 15.0% v/v |
| | 0.1 M Hydrochloric acid (to adjust pH to 7.6) | |
| | Polyethylene glycol 400 | 4.5% w/v |
| | Water for injection to 100% | |

| (f) | Injection II | (10 mg/ml) |
|---|---|---|
| | Compound X | 1.0% w/v |
| | Sodium phosphate BP | 3.6% w/v |
| | 0.1 M Sodium hydroxide solution | 15.0% v/v |
| | Water for injection to 100% | |

| (g) | Injection III | (1 mg/ml, buffered to pH 6) |
|---|---|---|
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

| (h) | Aerosol I | mg/ml |
|---|---|---|
| | Compound X | 10.0 |
| | Sorbitan trioleate | 13.5 |
| | Trichlorofluoromethane | 910.0 |
| | Dichlorodifluoromethane | 490.0 |

| (i) | Aerosol II | mg/ml |
|---|---|---|
| | Compound X | 0.2 |
| | Sorbitan trioleate | 0.27 |
| | Trichlorofluoromethane | 70.0 |
| | Dichlorodifluoromethane | 280.0 |
| | Dichlorotetrafluoroethane | 1094.0 |

| (j) | Aerosol III | mg/ml |
|---|---|---|
| | Compound X | 2.5 |
| | Sorbitan trioleate | 3.38 |
| | Trichlorofluoromethane | 67.5 |
| | Dichlorodifluoromethane | 1086.0 |
| | Dichlorotetrafluoroethane | 191.6 |

| (k) | Aerosol IV | mg/ml |
|---|---|---|
| | Compound X | 2.5 |
| | Soya lecithin | 2.7 |
| | Trichlorofluoromethane | 67.5 |
| | Dichlorodifluoromethane | 1086.0 |
| | Dichlorotetrafluoroethane | 191.6 |

| (l) | Ointment | ml |
|---|---|---|
| | Compound X | 40 mg |
| | Ethanol | 300 µl |
| | Water | 300 µl |
| | 1-Dodecylazacycloheptan-2-one | 50 µl |
| | Propylene glycol | to 1 ml |

Note

The above formulations may be obtained by conventional procedures well known in the pharmaceutical art. The tablets (a)–(c) may be enteric coated by conventional means, for example for example to provide a coating of cellulose-acetate phthalate. The aerosol formulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

What is claimed is:

1. A compound of the formula B:

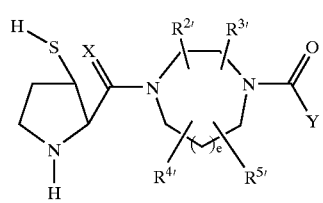

wherein:

X is O or H$_2$;

e is 0;

t is 1 to 4;

$R^{2'}$, $R^{3'}$, $R^{4'}$, and $R^{5'}$ are independently selected from: H; $C_{1-8}$alkyl, alkenyl, alkynyl, aryl, heterocycle, —CO—NR$^{6'}$R$^{7'}$ or —CO—OR$^{6'}$, unsubstituted or substituted with one or more of:

1) aryl or heterocycle, unsubstituted or substituted with:
   a) $C_{1-4}$alkyl,
   b) $(CH_2)_rOR^{6'}$,
   c) $(CH_2)_rNR^{6'}R^{7'}$,
   d) halogen,
2) $C_{3-6}$cycloalkyl,
3) $OR^{6'}$,
4) $SR^{6'}$, $S(O)R^{6'}$, $SO_2R^{6'}$,
5) $-NR^{6'}R^{7'}$,
6) $-NR^{6'}-CO-R^{7'}$,
7) $-NR^{6'}-CO-NR^{7'}R^{8'}$,
8) $-O-CO-NR^{6'}R^{7'}$,
9) $-O-CO-OR^{6'}$,
10) $-O-NR^{6'}R^{7'}$,
11) $-SO_2NR^{6'}R^{7'}$,
12) $-NR^{6'}-SO_2-R^{7'}$,
13) $-CO-R^{6'}$, or
14) $-CO-OR^{6'}$;

and any two of $R^{2'}$, $R^{3'}$, $R^{4'}$, and $R^{5'}$ are optionally attached to the same carbon atom;

Y is aryl, heterocycle, unsubstituted or substituted with one or more of:
1) $C_{1-4}$alkyl, unsubstituted or substituted with:
   a) $C_{1-4}$alkoxy,
   b) $NR^{6'}R^{7'}$,
   c) $C_{3-6}$cycloalkyl,
   d) aryl or heterocycle,
   e) HO,
2) aryl or heterocycle,
3) halogen,
4) $OR^{6'}$,
5) $NR^{6'}R^{7'}$,
6) CN,
7) $NO_2$, or
8) $CF_3$;

$R^{6'}$, $R^{7'}$ and $R^{8'}$ are independently selected from: H; $C_{1-4}$alkyl, $C_{3-6}$cycloalkyl, heterocycle, aryl, aroyl, heteroaroyl, arylsulfonyl, heteroarylsulfonyl, unsubstituted or substituted with:
   a) $C_{1-4}$alkoxy,
   b) aryl or heterocycle,
   c) halogen,
   d) HO,
   e) $-CO-R^{9'}$,
   f) $-SO_2R^{9'}$, wherein $R^{6'}$ and $R^{7'}$ may be joined in a ring, and
$R^{7'}$ and $R^{8'}$ may be joined in a ring;
$R^{9'}$ is $C_{1-4}$alkyl or aralkyl;
a pharmaceutically acceptable salt thereof.

2. The compound (2S)- 2-(2-methoxy- ethyl)-1-((cis)-3-sulfanyl-pyrrolidin-2-ylmethyl)-4-naphthoyl-piperazine or a pharmaceutically acceptable salt thereof.

3. A pharmaceutical composition which comprises a compound according to claim 1 or 2 and a pharmaceutically-acceptable carrier.

4. A process for preparing compounds of the Formula B as defined in claim 1 which comprises deprotecting a compound of Formula VI:

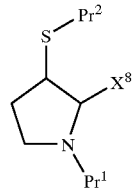

Formula VI wherein $X^8$ represents the right hand side of the Formula B as defined in claim 1, $Pr^1$ is H or an amino protecting group, $Pr^2$ is H or a thio protecting group and any functional groups in $X^8$ are optionally protected with the proviso that there is at least one protecting group and optionally, if desired, converting the product thus obtained into a pharmaceutically-acceptable salt thereof.

5. A method of treating a disease or medical condition mediated through farnesylation of CAAX-containing proteins which comprises administering to a warm-blooded animal an effective amount of a compound according to claim 1 or 2, wherein said disease or medical condition is carcinoma of the bladder, breast, colon, kidney, liver, lung, ovary, pancreas, stomach, cervix, thyroid or skin.

6. A method of treating a disease or medical condition mediated through farnesylation of CAAX-containing proteins which comprises administering to a warm-blooded animal an effective amount of a compound according to claim 1 or 2, wherein said disease or medical condition is a hematopoietic tumor of lymphoid lineage selected from acute lymphocytic leukemia, B-cell lymphoma and Burketts lymphoma.

7. A method of treating a disease or medical condition mediated through farnesylation of CAAX-containing proteins which comprises administering to a warm-blooded animal an effective amount of a compound according to claim 1 or 2, wherein said disease or medical condition is a hematopoietic tumor of myeloid lineage selected from acute or chronic myelogenous leukemias and promyelocytic leukemia.

8. A method of treating a disease or medical condition mediated through farnesylation of CAAX-containing proteins which comprises administering to a warm-blooded animal an effective amount of a compound according to claim 1 or 2, wherein said disease or medical condition is a tumor of mesenchymal origin selected from fibrosarcoma and rhabdomyosarcoma.

9. A method of treating a disease or medical condition mediated through farnesylation of CAAX-containing proteins which comprises administering to a warm-blooded animal an effective amount of a compound according to claim 1 or 2, wherein said disease or medical condition is a tumor selected from melanoma, seminoma, teratocarcinoma, neuroblastoma and glioma.

* * * * *